(12) United States Patent
Anémian et al.

(10) Patent No.: US 9,682,958 B2
(45) Date of Patent: Jun. 20, 2017

(54) LIGANDS AND THEIR PREPARATION

(71) Applicant: Merck Patent GmbH, Darmstadt (DE)

(72) Inventors: Rémi Manouk Anémian, Seoul (KR); Jong-Hyub Paek, Anjung (KR)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 14/416,481

(22) PCT Filed: Jun. 27, 2013

(86) PCT No.: PCT/EP2013/001890
§ 371 (c)(1),
(2) Date: Jan. 22, 2015

(87) PCT Pub. No.: WO2014/015936
PCT Pub. Date: Jan. 30, 2014

(65) Prior Publication Data
US 2015/0175574 A1 Jun. 25, 2015

(30) Foreign Application Priority Data
Jul. 23, 2012 (EP) .................................... 12005351

(51) Int. Cl.
C07D 401/00 (2006.01)
C07D 401/14 (2006.01)
C07D 213/38 (2006.01)

(52) U.S. Cl.
CPC ......... *C07D 401/14* (2013.01); *C07D 213/38* (2013.01)

(58) Field of Classification Search
None
See application file for complete search history.

(56) References Cited

U.S. PATENT DOCUMENTS

| 7,442,797 | B2 * | 10/2008 | Itoh ...................... C07D 213/06 313/504 |
| 2006/0202197 | A1 | 9/2006 | Nakayama et al. |
| 2007/0103060 | A1 | 5/2007 | Itoh et al. |
| 2008/0036373 | A1 | 2/2008 | Itoh et al. |
| 2010/0331293 | A1 | 12/2010 | Cushing et al. |
| 2012/0142708 | A1 | 6/2012 | Selness et al. |

FOREIGN PATENT DOCUMENTS

| JP | 2006/232784 | 9/2006 |
| JP | 2008-37848 | 2/2008 |
| WO | WO02/47690 A1 | 6/2002 |
| WO | WO2004/030672 A1 | 4/2004 |
| WO | WO2005/042444 | 5/2005 |
| WO | WO-2012/163471 A1 | 12/2012 |

OTHER PUBLICATIONS

Zheng, Z et al. New J Chem 2008 vol. 32 pp. 2150-2158.*
Chrisman et al., "Synthesis and Mutagenic Potency of Structural Isomers of 2-Amino-1-methyl-6-phenylimidazo[4,5-b]pyridine", J. Heterocyclic Chem., 2008, vol. 45, pp. 1641-1649.
Fallahpour et al., "Solvent-Free Synthesis of Bis(2,2':6'2"-terpyridin-4'-yl)amine and Its Metal Complexes", Synthesis, 2008, No. 10, pp. 1514-1516.
Huo et al., "Novel Phosphorecent Tetradentate Bis-cyclometalated CC*NN-coordinated Platinum Complexes: Structure, Photophysics, and a Synthetic Adventure", Polyhedron, 2013, vol. 52, pp. 1030-1040.
Sirisoma et al., "Discovery of Substituted 4-Anilino-2-arylpyrimidines as a New Series of Apoptosis Inducers Using a Cell- and Caspase-Based High Throughput Screening Assay. 2. Structure-Activity Relationships of the 2-Aryl group", Bioorganic & Medicinal Chemistry Letters, 2009, vol. 19, pp. 2305-2309.
Zheng et al., "Synthesis of New Dipyridinylamine and Dipyridinylmethane Ligands and their Coordination Chemistry with Mg(II) and Zn(II)", New Journal of Chemistry, 2008, vol. 32, pp. 2150-2158.
International Search Report for PCT/EP2013/001890; International Filing Date: Jun. 27, 2013.
English translation of Japanese Office Action, mailed Mar. 13, 2017, for Japanese Patent Application No. JP2015-523435, 8 pages.
Yoshiaki Fukushima, et al., Derivatives of Ditriazinylamine, Bulletin of the Chemical Society of Japan, vol. 44, pp. 794-798 (1971).
RN 1400064-88-1; Registry, Database Registry [Online] Retrieved from STN, Oct. 8, 2012, 5,6,7,8-tetrahydro-7-methyl-4-phenyl-N-(4-phenyl-2-pyrimidinyl)-[1]Benzothieno[2,3-d]pyrimidin-2-amine.
RN 1400024-37-4; Registry, Database Registry [Online] Retrieved from STN, Oct. 8, 2012, 6-chloro-4-phenyl-N-(4-phenyl-2-pyrimidinyl)-2-Quinazolinamine.
RN 1349753-75-8; Registry, Database Registry [Online] Retrieved from STN, Dec. 6, 2011, 2-(2-pyridinyl)-6-(3-pyridinyl)-N-[3-(5-pyrimidinyl)phenyl]-4-Pyrimidinamine.
RN 1349659-21-7; Registry, Database Registry [Onlin] Retrieved from STN, Dec. 6, 2011, N43-(2-methyl-4-pyrimidinyl)phenyl]-2-(2-pyridinyl)-6-(3-pyridinyl)-4-Pyrirnidinamine.
RN 1348139-24-1; Registry, Database Registry [Online]; Retrieved from STN, Dec. 4, 2011, 2-(2-pyridinyl)-6-(3-pyridinyl)-N-[3-(4-pyridinyl)phenyl]-4-Pyrimidinamine.
RN 667431-16-5; Registry, Database Registry [Online]; Retrieved from STN, Mar. 25, 2004, 6-chloro-4-phenyl-N-(5,6,7,8-tetrahydro-4-phenyl-2-quinazolinyl)-2-Quinazolinamine.
RN 1349065-85-5; Registry, Database Registry [Online]; Retrieved from STN, Dec. 5, 2011, N-[6-(pyridine-3-y1)-2-pyridinyl]-6-(2-thiazolyl)-3-methoxy-2-Pyridinamine.
RN 1026437-98-8; Registry, Database Registry [Online]; Retrieved from STN, Jun. 8, 2008, N-[3-(1H-indol-6-yl)phenyl]-4-(2-thiazolyl)-2-Pyrimidinamine.
RN 867302-70-3; Registry, Database Registry [Online]; Retrieved from STN, Nov. 11, 2005, 5,6,7,8-tetrahydro-N43-(6,7,8,9-tetrahydro-5H-1,2,4-triazolo[4,3-a]azepin-3-yl]phenyl]-2-(2-thienyl)-[1]Benzothieno[2,3-d]pyrirnidin-4-amine.

(Continued)

*Primary Examiner* — Heidi Reese
(74) *Attorney, Agent, or Firm* — RatnerPrestia

(57) ABSTRACT

The present invention relates to secondary amines suitable for the preparation of ligands for organometallic complexes, their preparation and their use.

3 Claims, No Drawings

(56) References Cited

OTHER PUBLICATIONS

RN 689751-78-8; Registry, Database Registry [Online]; Retrieved from STN, Jun. 6, 2004, 6-chloro-4-phenyl-N44-(2-thieny1)-6-(trifluoromethyl)-2-pyrimidinyl]-2-Quinazolinamine.

RN 1348432-08-5; Registry, Database Registry [Online]; Retrieved from STN, Dec. 4, 2011, N-[3-[4-(5-methy1-2-furany1)-2-thiazolyl]pheny1]-2-(2-pyridinyI)-6-(3-pyridiny1)-4-Pyrimidinamine.

RN 28182-08-3; Registry, Database Registry [Online]; Retrieved from STN, Nov. 16, 1984, 1-amino-2-(2-benzothiazolyI)-4-[(5-chloro-2-pheny1-4-pyrimidinyl)amino]-9,10-Anthracenedione.

* cited by examiner

LIGANDS AND THEIR PREPARATION

RELATED APPLICATIONS

This application is a national stage application, filed pursuant to 35 U.S.C. §371, of PCT/EP2013/001890, filed Jun. 27, 2013, which claims the benefit of European Patent Application No. 12005351.7, filed Jul. 23, 2012, which is incorporated herein by reference in its entirety.

The present invention relates inter alia to new compounds, their preparation and their use for the preparation of organometallic complexes.

Organometallic complexes have attracted much attention in the past. They can be used in a variety of applications. One of the most prominent field of application is the use organometallic complexes in electronic devices, such as organic electroluminescent devices (OLEDs—organic light emitting diodes, PLEDs—polymer light emitting diodes), organic integrated circuits (O-ICs), organic field effect transistors (O-FETs), organic thin film transistors (O-TFTs), organic light emitting transistors (O-LETs), organic solar cells (O-SCs), organic optical detectors, organic photoreceptors, organic field quenching devices (O-FQDs), light emitting electrochemical cells (LECs, OLECs, LEECs) or organic laser diodes (O-Laser).

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials being employed here are increasingly organometallic complexes which exhibit phosphorescence instead of fluorescence (M. A. Baldo et al., Appl. Phys. Lett. 1999, 75, 4 6). For quantum-mechanical reasons, an up to four-fold increase in energy and power efficiency is possible using organometallic compounds as phosphorescence emitters.

In accordance with the prior art, the phosphorescent emitters employed in phosphorescent OLEDs are, in particular, iridium and platinum complexes, which are usually employed as cyclometallated complexes. The ligands here are frequently derivatives of phenylpyridine.

Further, it has been reported that an ortho-metalated platinum complexes with aryl pyridines as a ligand and with platinum as the metal is useful as a phosphorescent material (JP 2001-181617) and a platinum complex using a bi-aryl skeleton compound as a ligand has also be reported (JP 2002-175884, JP 4110173, JP 2006-232784).

WO 2005/042444 discloses a class of promising metal complexes, particularly platinum complexes, with good light emitting characteristics. The ligands comprise a bis-(phenyl-pyridin) amine core. However, the chemical synthesis of the core and the ligands has a low yield. In order to obtain an economically efficient process for mass production the yield of the preparation needs to be improved.

The principle concept of the synthesis route for the preparation of the ligand according to the prior art is shown below.

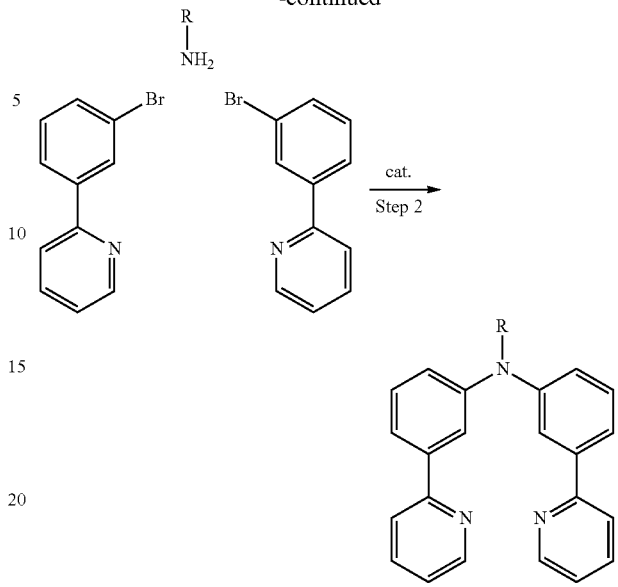

The conventional route is a two-step reaction with first formation of the primary amine and then formation of the desired ligand. Actually, step 2 covers two reactions that occur successively. At first, the primary amine R—$NH_2$ reacts with one of the two bromides yielding a secondary amine. The secondary amine then reacts, at least in part, with the second bromide in order to get the final product, which is a tertiary amine. However, the conversion of the secondary amine in step 2 into the product is, in many cases, not complete and the secondary amine can, therefore, be found as undesired side product in the reaction mixture. This lowers the overall yield of the reaction. Moreover, more elaborate purification of the product is required.

Furthermore, variation of the ligands is mainly due to the substituent R. Thus, for each R a new method for the preparation of R—$NH_2$ needs to be developed.

According to this conventional route the ligand and related ligands can be obtained with intermediate yields only. Unfortunately, by following this route only a limited number of different ligands is accessible.

The problem to be solved by the invention is, therefore, to provide a new synthesis route in order to obtain a large number of ligands for promising organic metallic complexes in high yield.

Surprisingly, a new synthesis route has been found that solve the problems of the prior art. The new process is very versatile and provides an easy access to a large number of ligands by employing different halogenated derivatives.

The new synthesis route is represented by a two step procedure. In the first step a secondary amine is prepared. This secondary amine represents the core ring structure of the ligand that is directly bound to the metal ion in the metal complex. In a second step the core structure is converted into a tertiary amine that represents the final ligand. This procedure allows to prepare a great number of ligands having different substitutions with surprisingly high yield. The following schema provides a simplified and exemplary view on the new route of preparation according to the present invention. The preparation of the core structure (step 1) can be optimized and standardized for a large amount of different ligands having different side groups R. The preparation of R-Hal can be accomplished easily by using standard techniques well known to the person skilled in the art. Via step 2 a large number of different ligands is then accessible. According to this procedure a large number of different ligands can be obtained in high yield. Furthermore, the process according to the present invention simplifies purification of the intermediates and products. Therefore, the process according to the present invention is suitable industrial application on large scale.

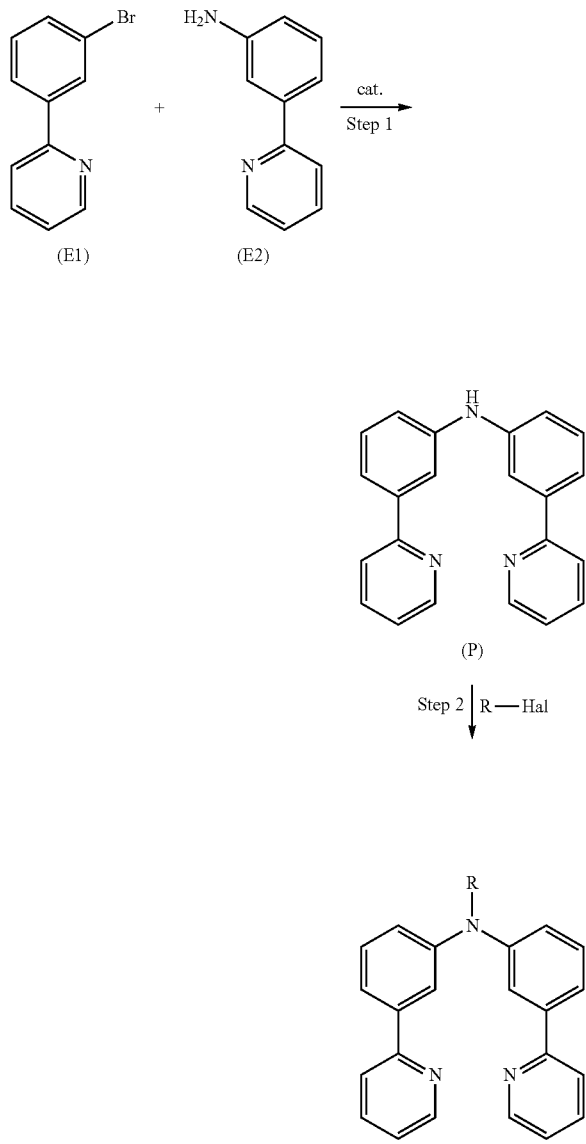

(E1)  (E2)

Step 1

(P)

Step 2 | R—Hal

The method for the preparation of the core structure and the ligand can be easily extended to different core structures.

The present invention relates to a process for the preparation of an aromatic/heteroaromatic secondary amine (P) through reaction of an aromatic/heteroaromatic primary amine (E2) with an aromatic/heteroaromatic halide (E1), wherein the reactants and products are defined below.

Thus, the present invention relates to a process for the preparation of a compound of Formula (3) comprising the reaction of a compound of Formula (1) with a compound of Formula (2)

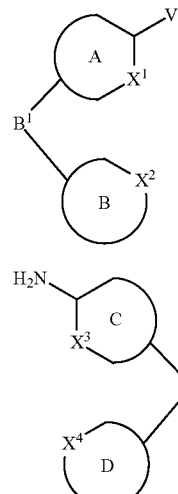

Formula (1)

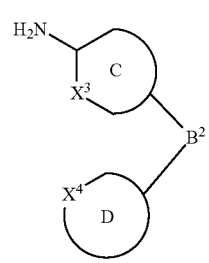

Formula (2)

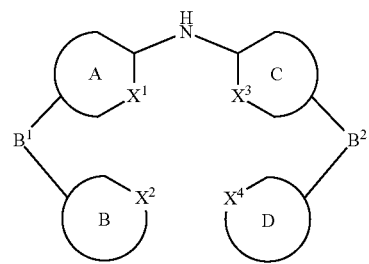

Formula (3)

wherein Formula (1), Formula (2) and Formula (3) correspond to E1, E2 and P, respectively, and where the following applies to the symbols and indices used:

A, B, C, D each represent an aromatic or heteroaromatic ring, condensed ring system or polycyclic ring system which may or may not be substituted with one or more rests $R^1$;

$X^1$, $X^2$, $X^3$, and $X^4$ are carbon atoms (C) or nitrogen atoms (N), wherein at least two out of $X^1$, $X^2$, $X^3$, and $X^4$ represent nitrogen atoms, preferably $X^1=C$, $X^2=N$, $X^3=C$ and $X^4=N$ or
$X^1=N$, $X^2=C$, $X^3=N$ and $X^4=C$ or
$X^1=N$, $X^2=C$, $X^3=C$ and $X^4=N$ or
$X^1=C$, $X^2=N$, $X^3=N$ and $X^4=C$ or
$X^1=N$, $X^2=N$, $X^3=C$ and $X^4=C$ or
$X^1=C$, $X^2=C$, $X^3=N$ and $X^4=N$, particularly preferably $X^1=C$, $X^2=N$, $X^3=C$ and $X^4=N$ or
$X^1=N$, $X^2=C$, $X^3=N$ and $X^4=C$ or and very particularly preferably $X^1=C$, $X^2=N$, $X^3=C$ and $X^4=N$;

$B^i$ (i=1 or 2)

are bridging units; the bridging units $B^i$ preferably represent, independently from each other, a single bond, rings, preferably 5-membered rings, comprising at least one N-atom, which are condensed to both neighboring rings, i.e. $B^1$ may be condensed to ring A and ring B or $B^2$ may be condensed to ring C and D, single bonds or bivalent atoms or groups, preferably $C(R^1)_2$, N—$R^1$, P—$R^1$, or Si—$(R^1)_2$, particularly preferably N—$R^1$, P—$R^1$, or Si—$(R^1)_2$, very particularly preferably $B^i$ represent a single bond between the rings A and B or C and D;

V is a leaving group, preferably a leaving group selected from Hal or $CF_3SO_3$, wherein Hal is a halogen selected from F, Cl, Br or I; Hal is preferably Br; preferably V is Br;

$R^1$
is, identically or differently on each occurrence, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, $B(R^2)_2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^2$, where one or more non-adjacent $CH_2$ groups may be replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$, or a combination of two or more of these groups; two or more radicals $R^1$ here may also form a mono- or polycyclic, aliphatic, aromatic and/or benzo-fused ring system with one another;

$R^2$
is, identically or differently on each occurrence, H, D, F, Cl, Br, I, $N(R^3)_2$, CN, $NO_2$, $Si(R^3)_3$, $B(OR^3)_2$, $C(=O)R^3$, $P(=O)(R^3)_2$, $S(=O)R^3$, $S(=O)_2R^3$, $OSO_2R^3$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^3$, where one or more non-adjacent $CH_2$ groups may be replaced by $R^3C=CR^3$, $C\equiv C$, $Si(R^3)_2$, $Ge(R^3)_2$, $Sn(R^3)_2$, $C=O$, $C=S$, $C=Se$, $C=NR^3$, $P(=O)(R^3)$, SO, $SO_2$, $NR^3$, O, S or $CONR^3$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^3$, or an aryloxy or heteroaryloxy group having 5 to 60 aromatic ring atoms, which may be substituted by one or more radicals $R^3$, or a diarylamino group, diheteroarylamino group or arylheteroarylamino group having 10 to 40 aromatic ring atoms, which may be substituted by one or more radicals $R^3$, or a combination of two or more of these groups; two or more adjacent radicals $R^2$ here may form a mono- or polycyclic, aliphatic or aromatic ring system with one another;

$R^3$
is, identically or differently on each occurrence, H, D, F or an aliphatic, aromatic and/or heteroaromatic hydrocarbon radical having 1 to 20 C atoms, in which, in addition, one or more H atoms may be replaced by F; two or more substituents $R^3$ here may also form a mono- or polycyclic, aliphatic or aromatic ring system with one another;

The reaction is carried out in the presence of a catalyst, preferably a metal metal or transition metal catalyst, particularly preferably a copper catalyst or a palladium catalyst, very particularly preferably a palladium catalyst and even more preferably a catalyst selected from $[PdCl(allyl)]_2$, $Pd_2(dba)_3$ and $Pd(OAc)_2$. Particular preference is given to $Pd(OAc)_2$ as catalyst. As co-ligand (or pre-catalyst) phosphines can be used, preferably diphenylphosphinoferrocene (dppf) can be used as co-ligand.

The reaction temperature is typically in the range between 30 and 200° C., preferably between 50 and 150° C., particularly preferably between 80 and 120° C.

However, other temperatures are also possible, since the reaction temperature depends on the solvent used. The reaction is carried out under reflux and the reaction temperature depends on the reflux temperature of the solvent.

The reaction time is between 3 and 64 hrs, preferably between 5 and 48 hrs, particularly preferably between 8 and 24 hrs and very particularly preferably the reaction time is between 12 and 20 hrs. Particular preference is given to a reaction time of ca. 16 hrs.

A wide range of organic solvents can be used for the process according to the present invention. Principally all organic solvents that are typically used in organic reactions can be employed. The solvent depends on the educts and products of the specific reaction. One skilled in the art will have no difficulties to select an appropriate solvent for the specific reaction according to the present invention. One preferred organic solvent is THF and one further preferred organic solvent that can be used in toluene.

The reaction is carried out in the presence of a base. The base employed depends on the specific educts and the other components of the reaction mixture. One person skilled in the art would have no problem to choose an appropriate base. Sodium tert.-butoxide, cesium carbonate, potassium phosphate or sodium hydroxide represent some selected bases that can be used, but other weaker or stronger bases can be used. Particular preference is given to sodium tert.-butoxide.

Preferably the present invention relates to a process for the preparation of a compound of Formula (6) comprising the reaction of a compound of Formula (4) with a compound of Formula (5)

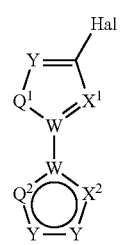

Formula (4)

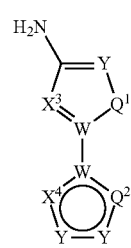

Formula (5)

Formula (6)

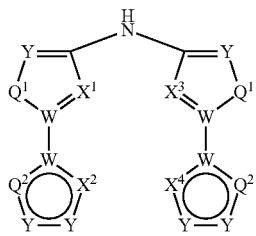

wherein Hal, $X^1$, $X^2$, $X^3$ and $X^4$ are defined as above and wherein the circle denotes aromaticity of the ring and wherein Y
is identically or differently on each occurrence selected from N and $CR^1$, preferably Y is $CR^1$;

$Q^1$
is identically or differently on each occurrence selected from Y—Y, N or S, preferably Y—Y or N, and particularly preferably Y—Y;

$Q^2$
is identically or differently on each occurrence selected from Y—Y, Y, N or S, preferably, wherein the groups in rings B and D are selected in that aromaticity is achieved;

W
is identically or differently on each occurrence selected from C and N, preferably W is C.

Particularly preferably the present invention relates to a process for the preparation of a compound of Formula (9) comprising the reaction of a compound of Formula (7) with a compound of Formula (8)

Formula (7)

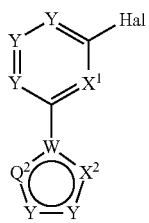

Formula (8)

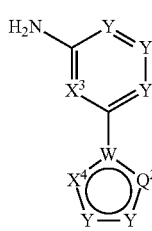

Formula (9)

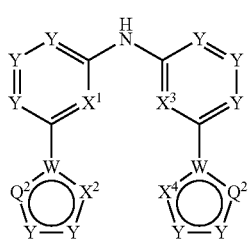

Very particularly preferably the present invention relates to a process for the preparation of a compound of Formula (12) comprising the reaction of a compound of Formula (10) with a compound of Formula (11)

Formula (10)

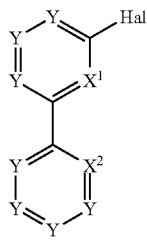

Formula (11)

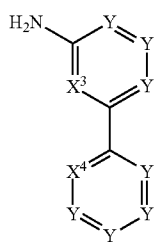

Formula (12)

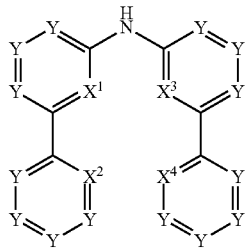

wherein the definitions for the groups as outlined above apply.

Very particularly preferably the present invention also relates to a process for the preparation of a compound of Formula (15) comprising the reaction of a compound of Formula (13) with a compound of Formula (14)

Formula (13)

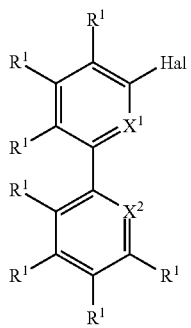

Formula (14)

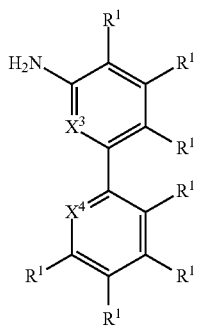

Formula (15)

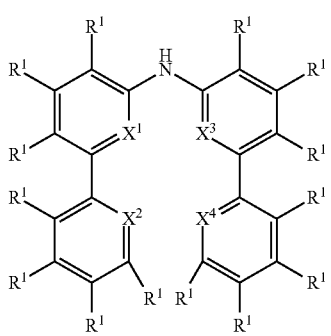

wherein the definitions for the groups as outlined above apply and wherein two or more rests R¹ can form, as outlined above, a ring.

Even more preferably the present invention also relates to a process for the preparation of a compound of Formula (18) comprising the reaction of a compound of Formula (16) with a compound of Formula (17)

Formula (16)

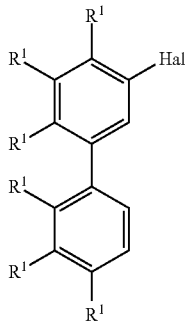

Formula (17)

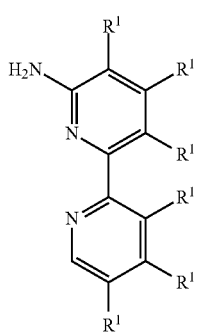

Formula (18)

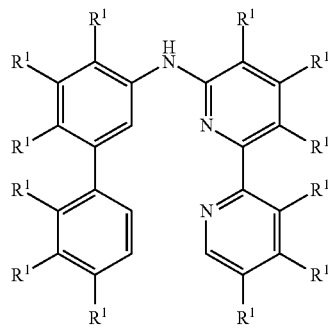

wherein the definitions for the groups as outlined above apply.

Even more preferably the present invention also relates to a process for the preparation of a compound of Formula (21) comprising the reaction of a compound of Formula (19) with a compound of Formula (20)

Formula (19)

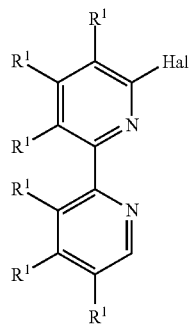

Formula (20)

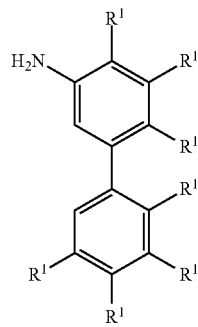

Formula (21)

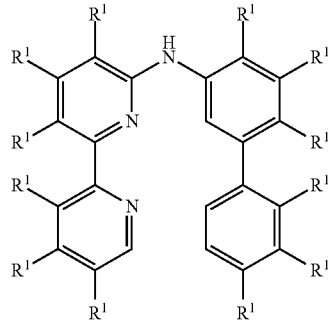

wherein the definitions for the groups as outlined above apply.

Even more preferably the present invention also relates to a process for the preparation of a compound of Formula (24) comprising the reaction of a compound of Formula (22) with a compound of Formula (23)

Formula (22)
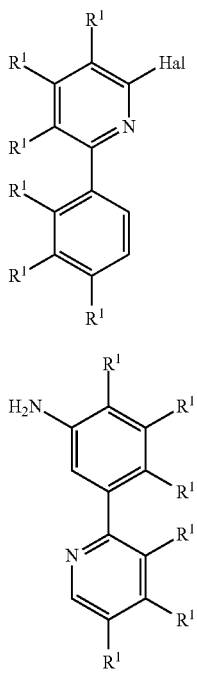

Formula (23)
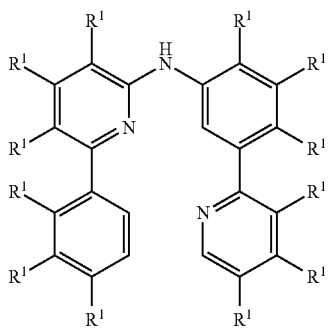

Formula (24)
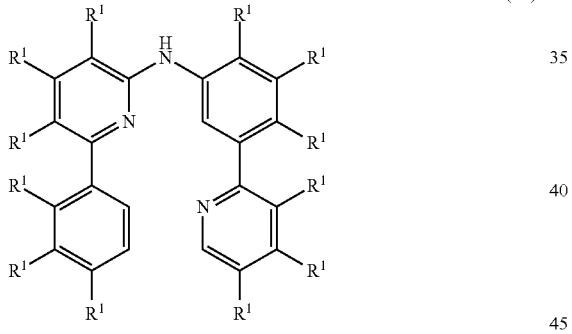

wherein the definitions for the groups as outlined above apply.

Even more preferably the present invention also relates to a process for the preparation of a compound of Formula (27) comprising the reaction of a compound of Formula (25) with a compound of Formula (26)

Formula (25)
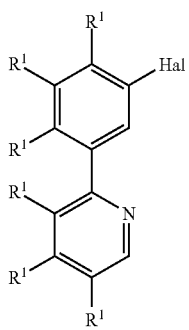

Formula (26)
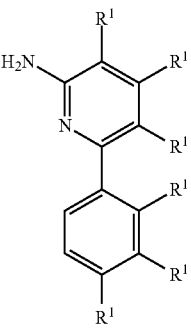

Formula (27)
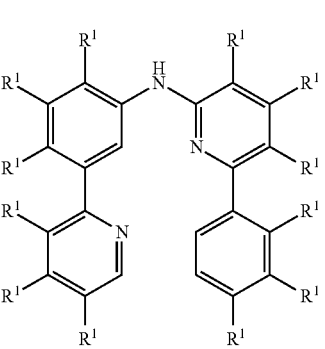

wherein the definitions for the groups as outlined above apply.

Even more preferably the present invention also relates to a process for the preparation of a compound of Formula (30) comprising the reaction of a compound of Formula (28) with a compound of Formula (29)

Formula (28)
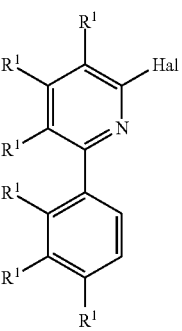

Formula (29)
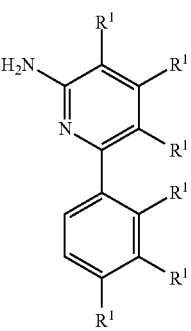

Formula (30)

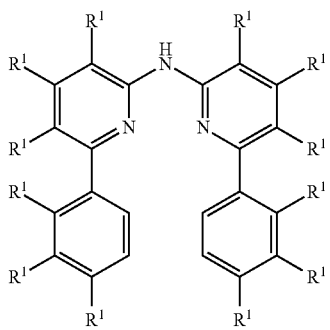

wherein the definitions for the groups as outlined above apply.

Even more preferably the present invention also relates to a process for the preparation of a compound of Formula (33) comprising the reaction of a compound of Formula (31) with a compound of Formula (32)

Formula (31)

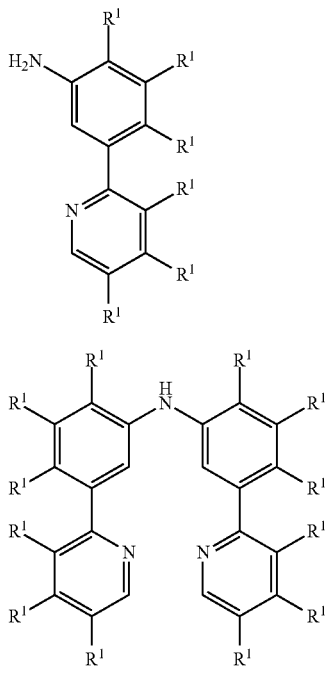

Formula (32)

Formula (33)

wherein the definitions for the groups as outlined above apply.

Preference is also given to a process for the preparation of a compound of Formula (36) comprising the reaction of a compound of Formula (34) with a compound of Formula (35)

Formula (34)

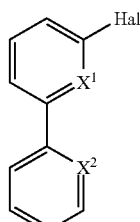

Formula (35)

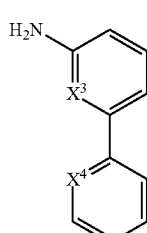

Formula (36)

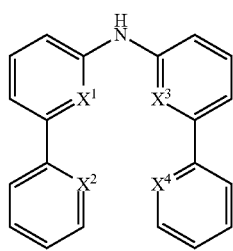

wherein the definitions for the groups as outlined above apply.

Preference is also given to a process for the preparation of a compound of Formula (39) comprising the reaction of a compound of Formula (37) with a compound of Formula (38)

Formula (37)

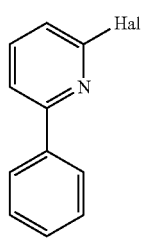

Formula (38)

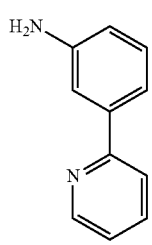

Formula (39)

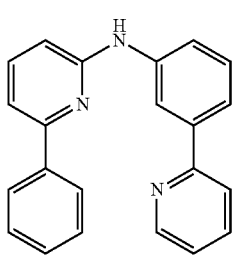

wherein the definition for Hal as outlined above applies.

Preference is also given to a process for the preparation of a compound of Formula (42) comprising the reaction of a compound of Formula (40) with a compound of Formula (41)

Formula (40)

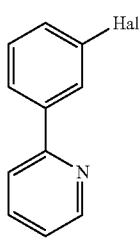

Formula (41)

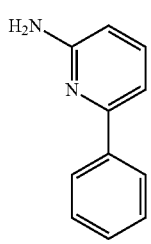

Formula (42)

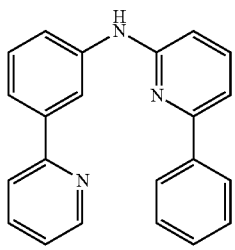

wherein the definition for Hal as outlined above applies.

Preference is also given to a process for the preparation of a compound of Formula (45) comprising the reaction of a compound of Formula (43) with a compound of Formula (44)

Formula (43)

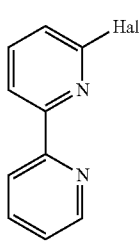

Formula (44)

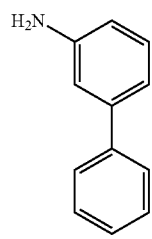

Formula (45)

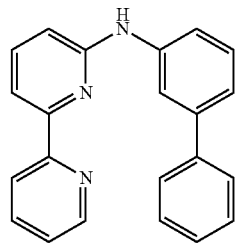

wherein the definition for Hal as outlined above applies.

Preference is also given to a process for the preparation of a compound of Formula (48) comprising the reaction of a compound of Formula (46) with a compound of Formula (47)

Formula (46)

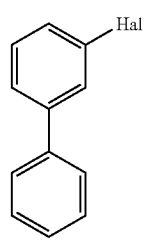

Formula (47)

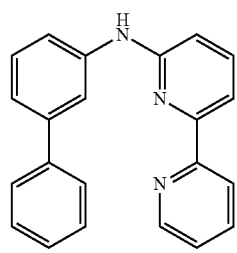

Formula (48)

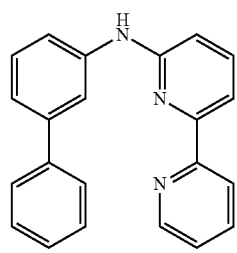

wherein the definition for Hal as outlined above applies.

Preference is also given to a process for the preparation of a compound of Formula (51) comprising the reaction of a compound of Formula (49) with a compound of Formula (50)

Formula (49)

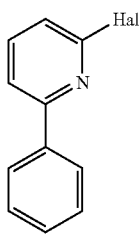

Formula (50)

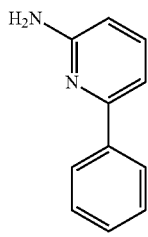

Formula (51)

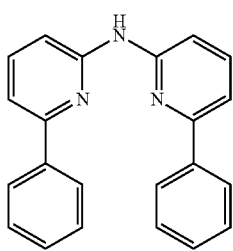

wherein the definition for Hal as outlined above applies.

Most preferably the present invention relates to a process for the preparation of a compound of Formula (54) comprising the reaction of a compound of Formula (52) with a compound of Formula (53)

Formula (52)

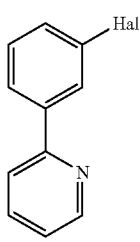

Formula (53)

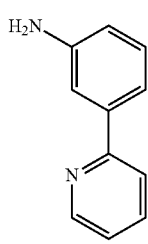

Formula (54)

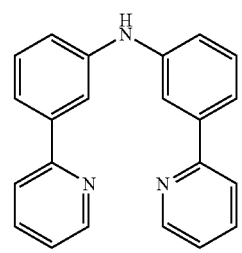

wherein the definition for Hal as outlined above applies.

The present invention also relates to a process for the preparation of a compound of Formula (57) comprising the reaction of a compound of Formula (55) with a compound of Formula (56)

Formula (55)

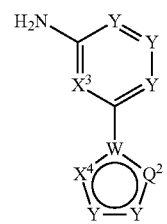

Formula (56)

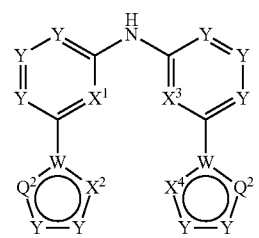

Formula (57)

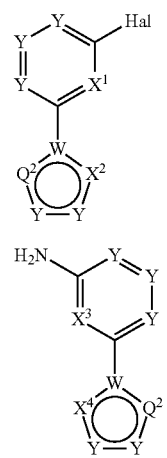

wherein the definitions for the groups as outlined above apply and wherein $Q^2$ is $CR^1$, N or S.

Preferably the present invention also relates to a process for the preparation of a compound of Formula (60) comprising the reaction of a compound of Formula (58) with a compound of Formula (59)

Formula (58)

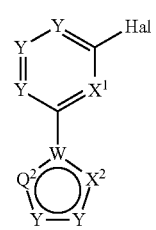

-continued

Formula (59)

Formula (60)

wherein the definitions for the groups as outlined above apply and wherein $Q^2$ is $CR^1$, N or S.

Particularly preferably the present invention also relates to a process for the preparation of a compound of Formula (63) comprising the reaction of a compound of Formula (61) with a compound of Formula (62)

Formula (61)

Formula (62)

Formula (63)

wherein the definitions for the groups as outlined above apply and wherein $Q^2$ is $CR^1$, N or S.

Particularly preferably the present invention also relates to a process for the preparation of a compound of Formula (66) comprising the reaction of a compound of Formula (64) with a compound of Formula (65)

Formula (64)

Formula (65)

Formula (66)

wherein the definitions for the groups as outlined above apply.

Preferably $R^1$ is, identically or differently on each occurrence, H, D, F, Cl, Br, I, $N(R^2)_2$, CN, $NO_2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$, where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$, or a combination of two or more of these groups; two or more radicals $R^1$ here may also form a mono- or polycyclic, aliphatic, aromatic and/or benzo-fused ring system with one another.

Particularly preferably $R^1$ is, identically or differently on each occurrence, D, F, Cl, Br, I, $N(R^2)_2$, CN, $NO_2$, a straight-chain alkyl or alkoxy group having 1 to 40 C atoms or a branched or cyclic alkyl or alkoxy group having 3 to 40 C atoms, each of which may be substituted by one or more radicals $R^2$, where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$; two or more radicals $R^1$ here may also form a mono- or polycyclic, aliphatic, aromatic and/or benzo-fused ring system with one another.

The following table covers some examples of compounds that can be prepared according to the present invention.

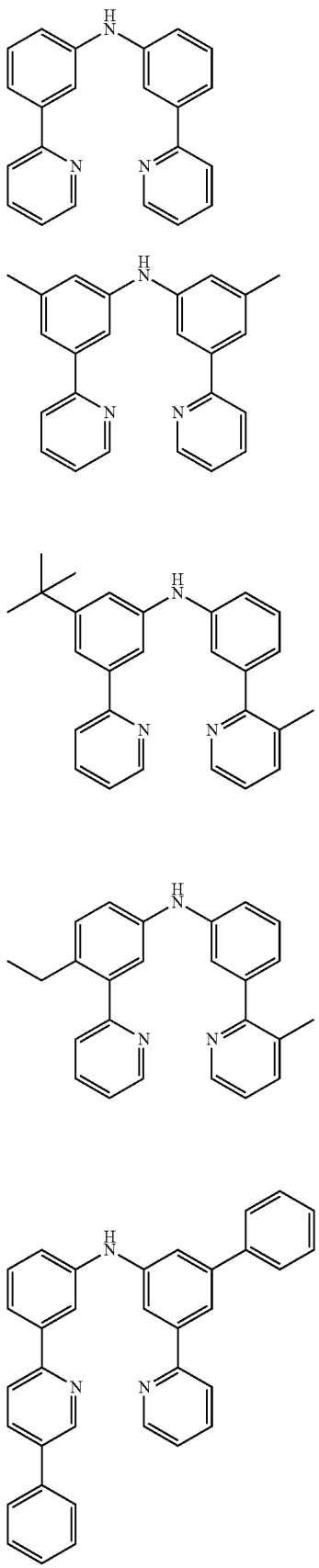
Formula (67)
Formula (68)
Formula (69)
Formula (70)
Formula (71)
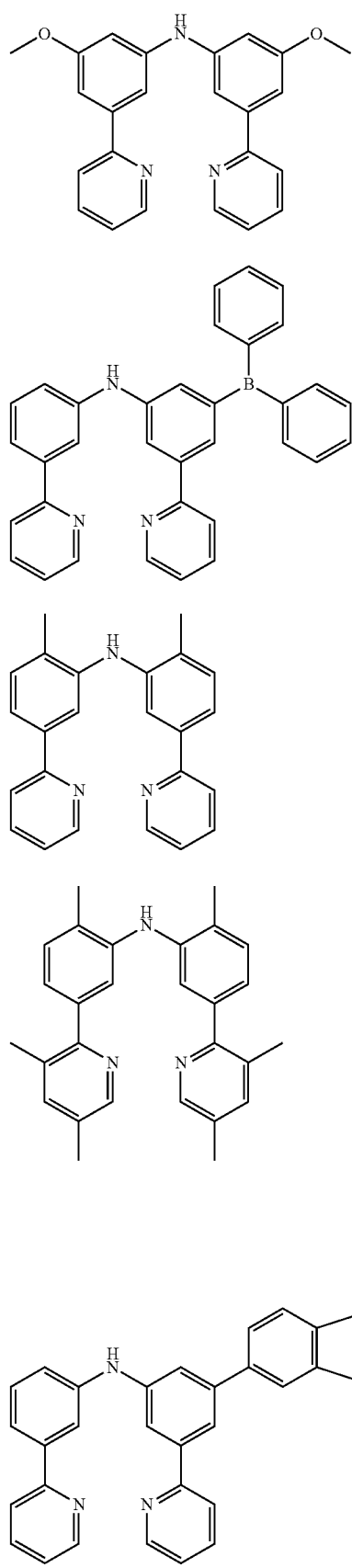
Formula (72)
Formula (73)
Formula (74)
Formula (75)
Formula (76)

Formula (77)
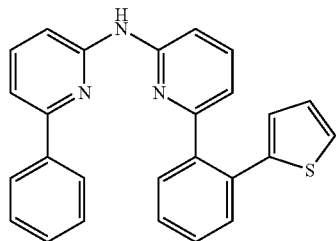
Formula (78)
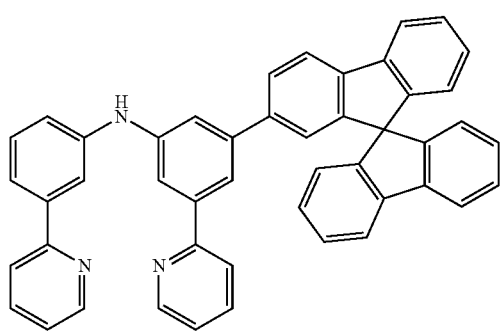
Formula (79)
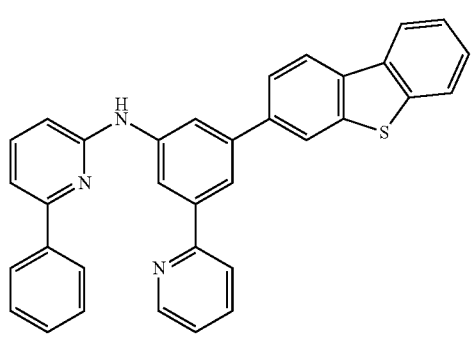
Formula (80)
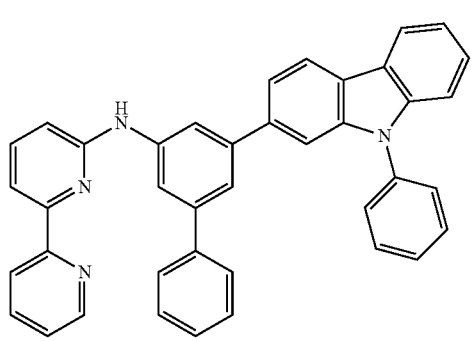
Formula (81)
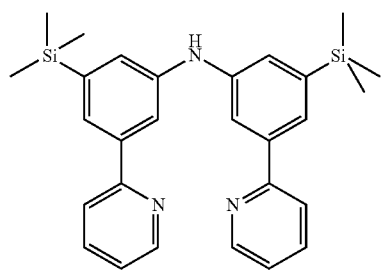
Formula (82)
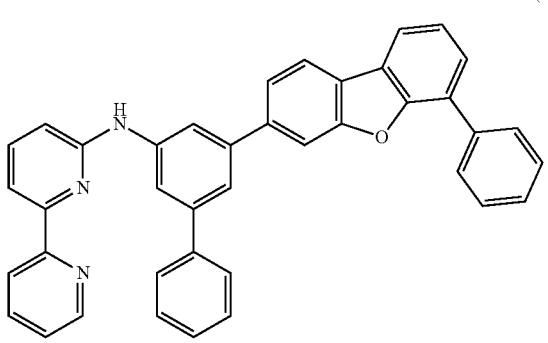
Formula (83)
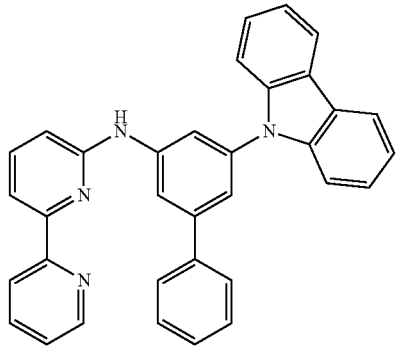
Formula (84)
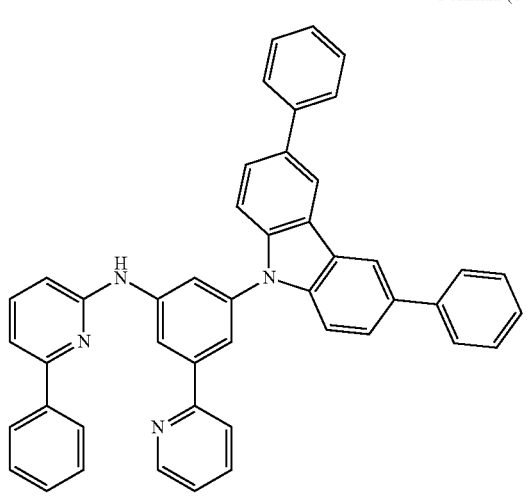
Formula (85)
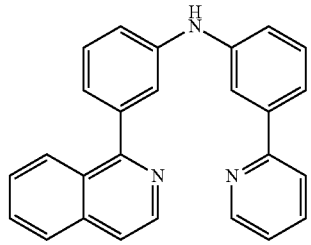

Formula (86)
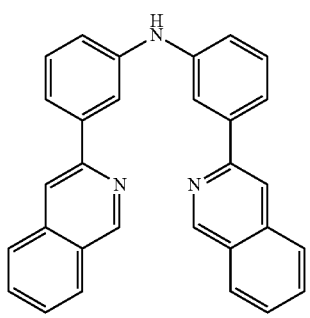
Formula (87)
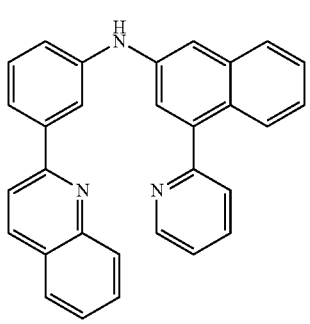
Formula (88)
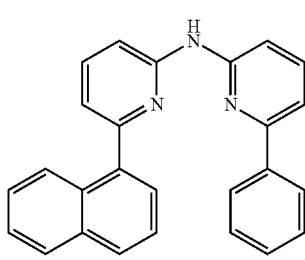
Formula (89)
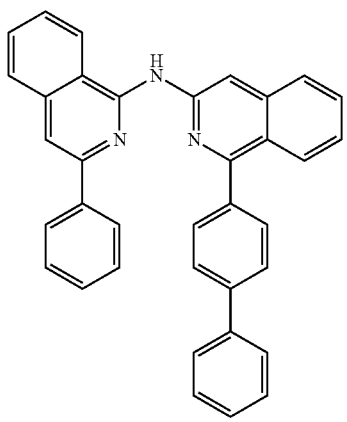
Formula (90)
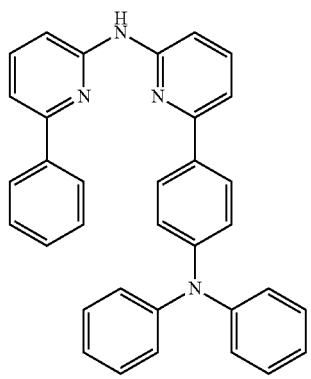
Formula (91)
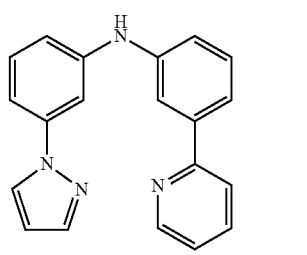
Formula (92)
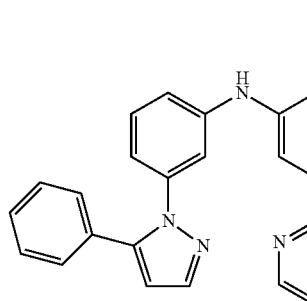
Formula (93)
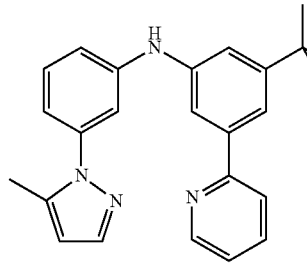
Formula (94)
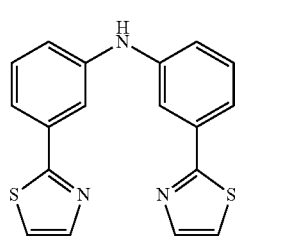

Formula (95)
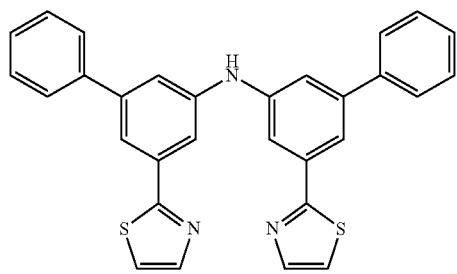
Formula (96)
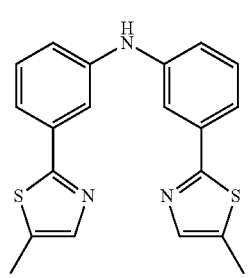
Formula (97)
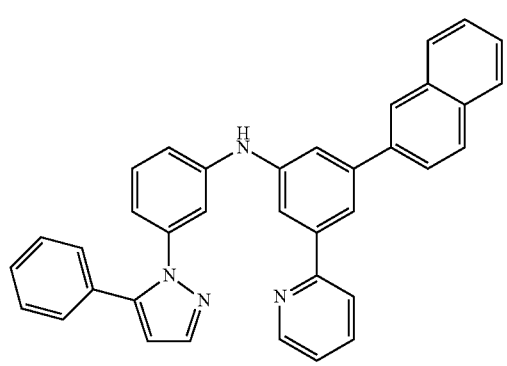
Formula (98)
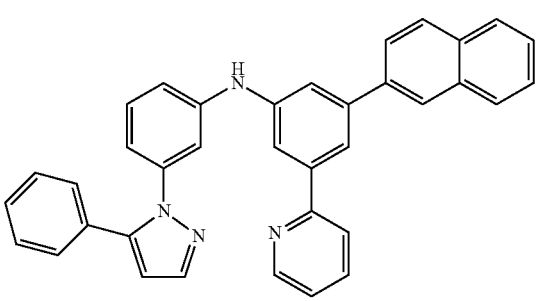
Formula (99)
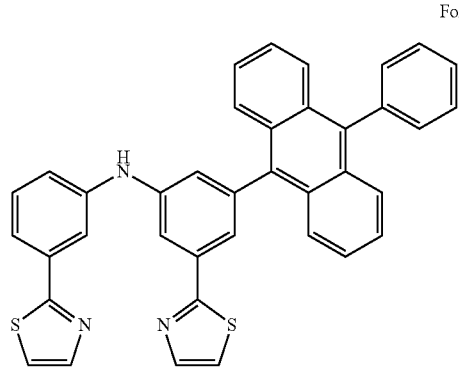
Formula (100)
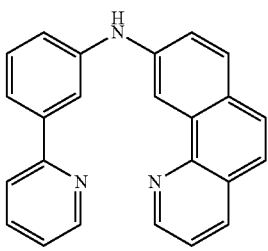
Formula (101)
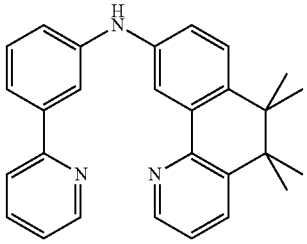
Formula (102)
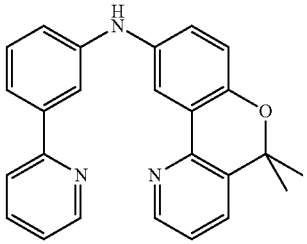
Formula (103)
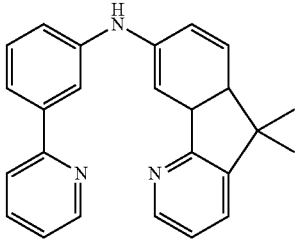
Formula (104)
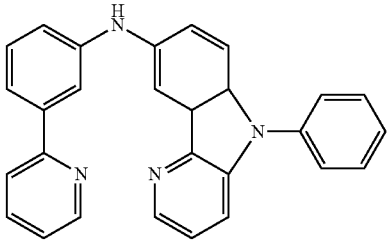
Formula (105)
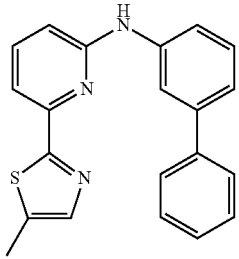

Formula (106)
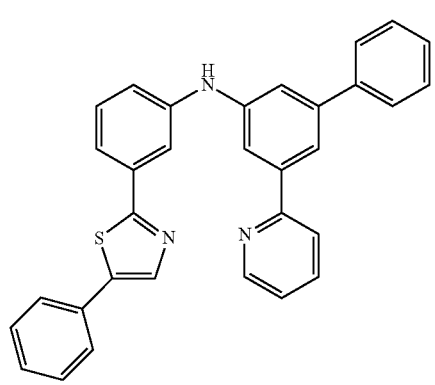
Formula (107)
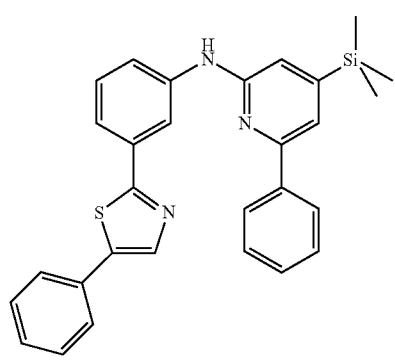
Formula (108)
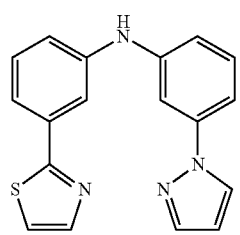
Formula (109)
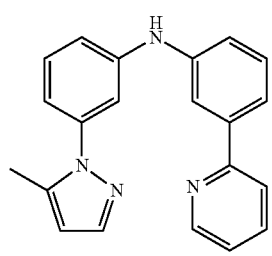
Formula (110)
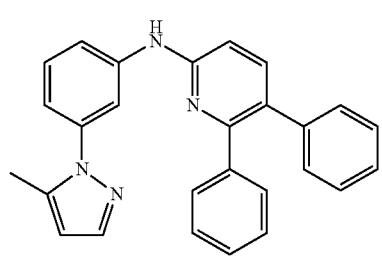
Formula (111)
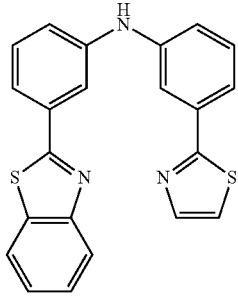
Formula (112)
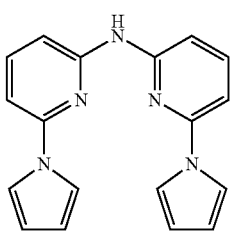
Formula (113)
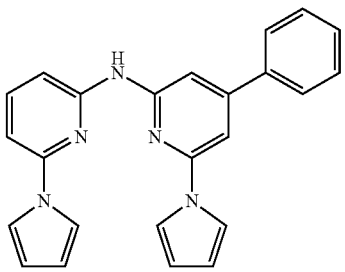
Formula (114)
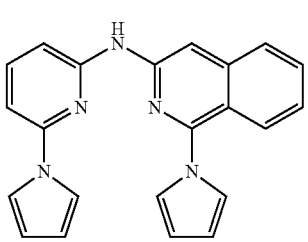
Formula (115)
Formula (116)
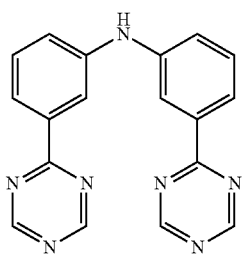

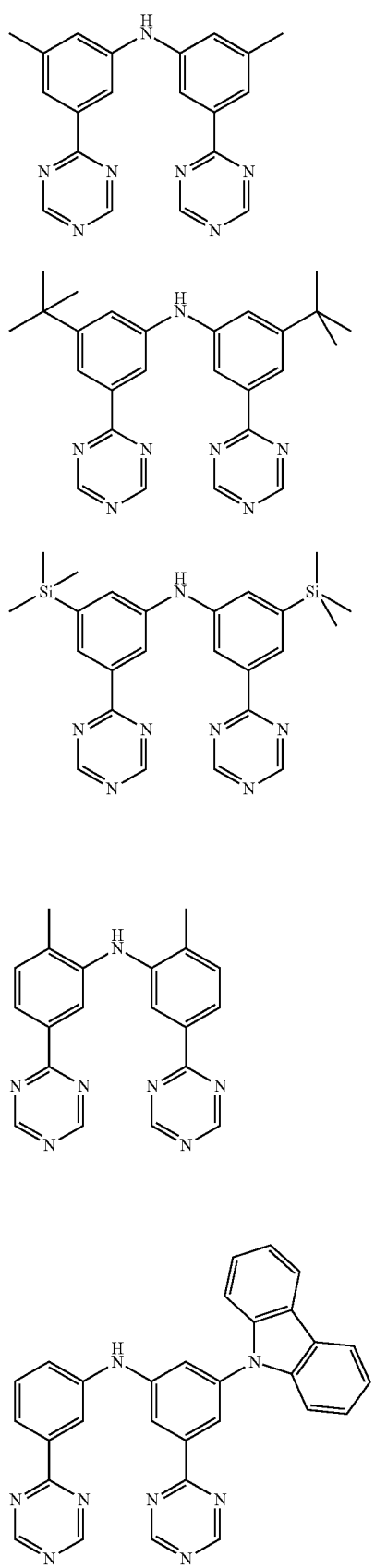
Formula (117)
Formula (118)
Formula (119)
Formula (120)
Formula (121)
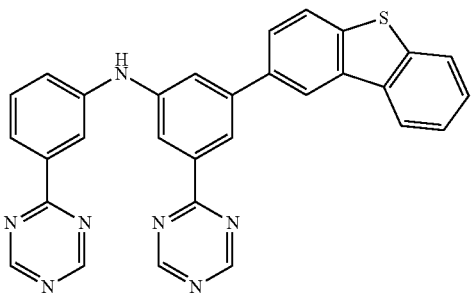
Formula (122)
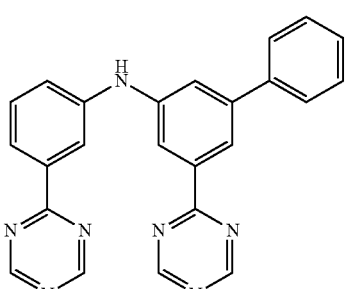
Formula (123)
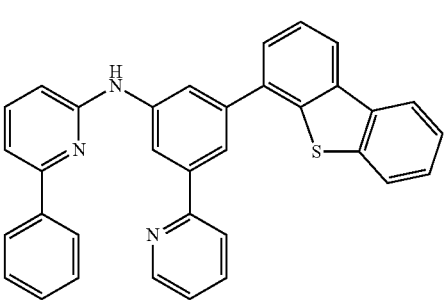
Formula (124)
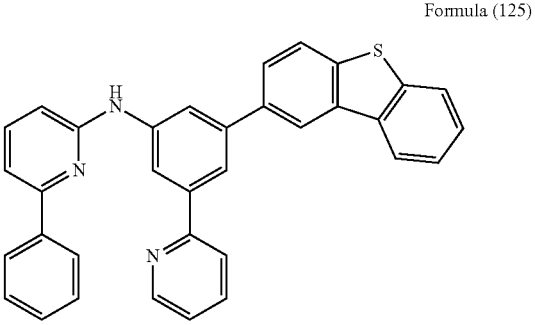
Formula (125)
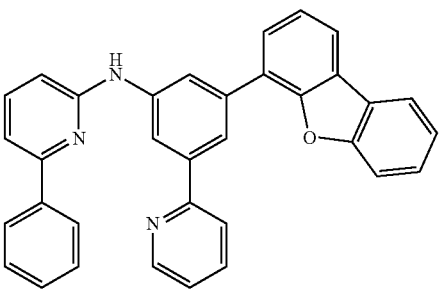
Formula (126)
The secondary amines prepared in the way as outlined above, such as the compound of Formula (3), can be used to prepare further derivatives that are tertiary amines. These tertiary amines can be used as ligands for metal complexes, that are highly promising for the use in organic electronics. As an example, metal complexes bearing these ligands are often employed in organic light emitting diodes (OLEDs) or in organic light emitting electrochemical cells (OLECs, LECs or LEECs) as light emitting compounds, particularly as phosphorescent compounds (EP 1683804).

Thus, the present invention relates to the use of the secondary amine compounds prepared as described above for the preparation of tertiary amines.

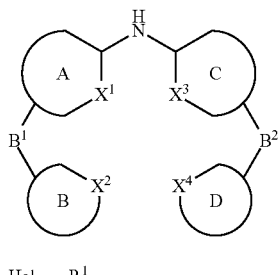

Formula (3)

Hal—R$^1$

Formula (127)

Formula (128)

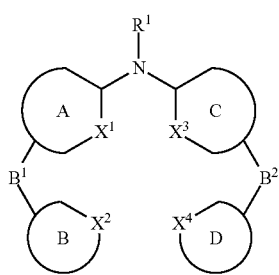

wherein the symbols are defined as above.

The reaction is carried out in the presence of a catalyst, preferably a metal metal or transition metal catalyst, particularly preferably a copper catalyst or a palladium catalyst, very particularly preferably a palladium catalyst and even more preferably a catalyst selected from [PdCl(allyl)]$_2$, Pd$_2$(dba)$_3$ and Pd(OAc)$_2$. Particular preference is given to Pd(OAc)$_2$ as catalyst. The reaction temperature is typically in the range between 30 and 200° C., preferably between 50 and 150° C., particularly preferably between 80 and 120° C. As co-ligand (or pre-catalyst) phosphines can be used, preferably used tri-tertbutyl phosphine is be used as co-ligand.

However, other temperatures are also possible, since the reaction temperature depends on the solvent used. The reaction is carried out under reflux and the reaction temperature depends on the reflux temperature of the solvent.

The reaction time is between 3 and 64 hrs, preferably between 5 and 48 hrs, particularly preferably between 8 and 24 hrs and very particularly preferably the reaction time is between 12 and 20 hrs. Particular preference is given to a reaction time of ca. 16 hrs.

A wide range of organic solvents can be used for the process according to the present invention. Principally all organic solvents that are typically used in organic reactions can be employed. The solvent depends on the educts and products of the specific reaction. One skilled in the art will have no difficulties to select an appropriate solvent for the specific reaction according to the present invention. One preferred organic solvent is THF and one further preferred organic solvent that can be used in toluene.

The reaction is preferably carried out in the presence of a base. The base employed depends on the specific educts and the other components of the reaction mixture. One person skilled in the art would have no problem to choose an appropriate base. Sodium tert.-butoxide, cesium carbonate, potassium phosphate or sodium hydroxide represent some selected bases that can be used, but other weaker or stronger bases can be used. Particular preference is given to sodium tert.-butoxide.

The tertiary amines can be used for the preparation of metal complexes is a transition metal or metal ion, preferably a metal or metal ion selected from the Platinum Group (i.e. Fe, Co, Ni, Ru, Rh, Pd, Os, Ir, Pt) or gold, particularly preferably from Pt(II), Pd(II), Ni(II), Rh(I), and Au(III), very particularly preferably from Pt(II), Ir(I) and Au(III) and even more preferably from Pt(II). The preparation of these metal complexes is well known to one skilled in the art. Examples for the preparation of platinum complexes are disclosed, e.g., in EP 1683804.

The present invention also relates to a compound having the general Formula (3)

Formula (3)

wherein the symbols have the meanings as defined above and wherein the preferred embodiments as defined above apply as well.

Preferably the present invention relates to a compound having the general Formula (9) wherein the symbols have the meanings as defined above and wherein the preferred embodiments as defined above apply as well.

Preferably the present invention also relates to a compound having the general Formula (12) wherein the symbols have the meanings as defined above and wherein the preferred embodiments as defined above apply as well.

Preferably the present invention also relates to a compound having the general Formula (15) wherein the symbols have the meanings as defined above and wherein the preferred embodiments as defined above apply as well.

Particularly preferably the present invention relates to a compound having the general Formula (18) wherein the symbols have the meanings as defined above and wherein the preferred embodiments as defined above apply as well.

Particularly preferably the present invention also relates to a compound having the general Formula (21) wherein the symbols have the meanings as defined above and wherein the preferred embodiments as defined above apply as well.

Particularly preferably the present invention also relates to a compound having the general Formula (24) wherein the symbols have the meanings as defined above and wherein the preferred embodiments as defined above apply as well.

Particularly preferably the present invention also relates to a compound having the general Formula (27) wherein the symbols have the meanings as defined above and wherein the preferred embodiments as defined above apply as well.

Very particularly preferably the present invention relates to a compound having the general Formula (30) wherein the symbols have the meanings as defined above and wherein the preferred embodiments as defined above apply as well.

Very particularly preferably the present invention also relates to a compound having the general Formula (33) wherein the symbols have the meanings as defined above and wherein the preferred embodiments as defined above apply as well.

Even more preferably the present invention relates to a compound having the general Formula (36) wherein the symbols have the meanings as defined above and wherein the preferred embodiments as defined above apply as well.

Even more preferably the present invention also relates to a compound having the general Formula (39).

Even more preferably the present invention also relates to a compound having the general Formula (42).

Even more preferably the present invention also relates to a compound having the general Formula (45).

Even more preferably the present invention also relates to a compound having the general Formula (48).

Even more preferably the present invention also relates to a compound having the general Formula (51).

Even more preferably the present invention also relates to a compound having the general Formula (54).

Preferably the present invention relates to a compound having the general Formula (57) wherein the symbols have the meanings as defined above and wherein the preferred embodiments as defined above apply as well.

Preferably the present invention relates to a compound having the general Formula (60) wherein the symbols have the meanings as defined above and wherein the preferred embodiments as defined above apply as well.

Preferably the present invention relates to a compound having the general Formula (63) wherein the symbols have the meanings as defined above and wherein the preferred embodiments as defined above apply as well.

Preferably the present invention relates to a compound having the general Formula (66) wherein the symbols have the meanings as defined above and wherein the preferred embodiments as defined above apply as well. Some selected preferred compounds according to the present invention are the compounds having the Formulae (67) to (126).

The present invention also relates to a formulation comprising at least one of the compounds according to the present invention and at least one solvent.

The compounds according to the present invention can be used, as outlined above, for the preparation of compounds that are useful as ligands for metal complexes.

An aryl group in the sense of this invention contains 6 to 40 C atoms; a heteroaryl group in the sense of this invention contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

An aromatic ring system in the sense of this invention contains 6 to 60 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, an $sp^3$-hybridised C, N or O atom or a carbonyl group. Thus, for example, systems such as 9,9'-spirobifluorene, 9,9-diarylfluorene, triarylamine, diaryl ether, stilbene, etc., are also intended to be taken to mean aromatic ring systems for the purposes of this invention, and likewise systems in which two or more aryl groups are interrupted, for example, by a linear or cyclic alkyl group or by a silyl group.

A cyclic alkyl, alkoxy or thioalkoxy group in the sense of this invention is taken to mean a monocyclic, bicyclic or polycyclic group.

For the purposes of the present invention, a $C_1$- to $C_{40}$-alkyl group, in which, in addition, individual H atoms or $CH_2$ groups may be substituted by the above-mentioned groups, is taken to mean, for example, the radicals methyl, ethyl, n-propyl, i-propyl, n-butyl, i-butyl, s-butyl, t-butyl, 2-methyl-butyl, n-pentyl, s-pentyl, tert-pentyl, 2-pentyl, cyclopentyl, n-hexyl, s-hexyl, tert-hexyl, 2-hexyl, 3-hexyl, cyclohexyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, trifluoromethyl, pentafluoroethyl or 2,2,2-trifluoroethyl. An alkenyl group is taken to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is taken to mean, for example, ethynyl, propynyl, butynyl, pentynyl, hexynyl, heptynyl or octynyl. A $C_1$- to $C_{40}$-alkoxy group is taken to mean, for example, methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system having 5-60 aromatic ring atoms, which may also in each case be substituted by the radicals R mentioned above and which may be linked to the aromatic or heteroaromatic ring system via any desired positions, is taken to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4, 5-tetrazine, 1,2,3,4-tetrazine, 1,2,3,5-tetrazine, purine, pteridine, indolizine and benzothiadiazole.

Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), comprising, in at least one layer, at least one compound of the Formula (1) indicated above. Particular preference is given to organic electroluminescent devices. Active components are generally the organic or inorganic materials, which are introduced between the anode and cathode, for example charge-injection, charge-transport or charge-blocking materials, but in particular emission materials and matrix materials. The compounds according to the invention exhibit particularly good properties as emission material in organic electroluminescent devices. Organic electroluminescent devices are therefore a preferred embodiment of the invention.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, charge-generation layers and/or organic or inorganic p/n junctions. It is likewise possible for interlayers, which have, for example, an exciton-blocking function and/or control the charge balance in the electroluminescent device, to be introduced between two emitting layers. However, it should be pointed out that each of these layers does not necessarily have to be present. The organic electroluminescent device may comprise one emitting layer or a plurality of emitting layers. If a plurality of emission layers are present, these preferably have in total a plurality of emission maxima between 300 nm and 800 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 2005/011013), or systems which comprise more than three emitting layers.

The preparation of the compounds according to the present invention is distinguished by the following surprising advantages over the prior art:
1. The preparation route provides a simple way to prepare compounds that are precursors of ligands;
2. The compounds can be obtained in surprisingly high yields. The costs of goods can be lowered by using the route according to the invention. Thus, the new synthesis route is suitable for commercial production of the compounds, even for mass production;
3. The new synthesis route offers a simple way to provide a large amount of derivatives. The process according to the present invention is, thus, a more versatile and efficient way to obtain ligands for organometallic complexes as compared to the route according to the prior art.
4. The process according to the present invention requires only easy purification of the intermediates and/or products, which results in higher yields and lower production costs.
5. The compounds can be obtained with high purity. High purity of ligands is required for high performance electronic and electroluminescent devices.

It should be pointed out that variations of the embodiments described in the present invention fall within the scope of this invention. Each feature disclosed in the present invention can, unless explicitly excluded, be replaced by alternative features which serve the same, an equivalent or a similar purpose. Thus, each feature disclosed in the present invention should, unless stated otherwise, be regarded as an example of a generic series or as an equivalent or similar feature.

All features of the present invention can be combined with one another in any way, unless certain features and/or steps are mutually exclusive. This applies, in particular, to preferred features of the present invention. Equally, features of non-essential combinations can be used separately (and not in combination).

It should furthermore be pointed out that many of the features, and in particular those of the preferred embodiments of the present invention, should be regarded as inventive themselves and not merely as part of the embodiments of the present invention. Independent protection may be granted for these features in addition or as an alternative to each invention claimed at present.

The teaching regarding technical action disclosed with the present invention can be abstracted and combined with other examples.

The invention is explained in greater detail by the following examples without wishing it to be restricted thereby.

WORKING EXAMPLES

The following syntheses are, unless indicated otherwise, carried out under a protective-gas atmosphere in dried solvents. Compound (I) can be prepared in accordance with Chem. Commun., 2010, 46, 3958 and compound (II) can be prepared according to WO 2007/000339. Compound (IV) can be prepared according to WO 2011/021689. Compounds (VIII), (IX), (XVII), (XXIII), (XXIV), (XXV), (XXIX), (XXXI) and (XXXII) are commercially available. Compound (XXII) can be prepared according to Inorg. Chem. 2011, 50, 8261. Compounds (XXVI) and (XXVII) can be prepared according to Inorg. Chem. 2010, 49, 5107. Compound (XXVIII) can be prepared according to Eur. J. Org. Chem. 2011, 1280. Compound (XXX) can be prepared according to Chem. Mater. 2011, 23, 4487.

Example 1

Preparation of Compound (III)

Synthetic Procedure for the Preparation of Compound (III)

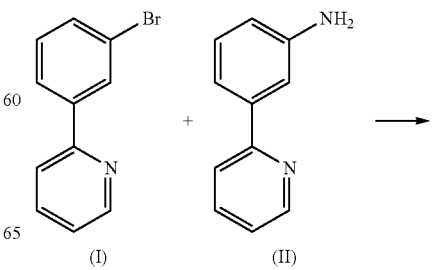

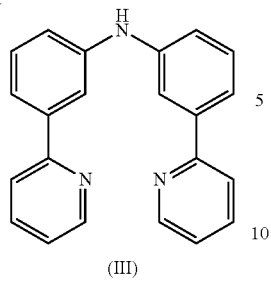

(III)

Preparation of Compound (III)

7.2 g (30.6 mmol) of compound (I) and 5.2 g (30.6 mmol) of compound (II) are suspended in 200 mL of toluene under Ar atmosphere. 340 mg (0.61 mmol) of 1,1-bis-(diphenyl-phosphino)-ferrocene and 140 mg (0.61 mmol) of Pd(OAc)₂ are added to the flask and stirred vigorously under Ar atmosphere. Then 3.5 g (36.7 mmol) of sodium t-butoxide is added to the flask under Ar. The reaction mixture is stirred under reflux for 24 h. After cooling to room temperature, the organic phase is separated off, washed three times with 100 mL of water, dried over magnesium sulfate, filtered and subsequently evaporated to dryness. The residue is purified by column chromatography on silica gel using a mixture of ethylacetate/heptane (1:2). The yield is 82 g (29.4 mmol), corresponding to 96% of theory.

Example 2

Preparation of Compound (VI)

Synthetic Procedure for the Preparation of Compound (VI)

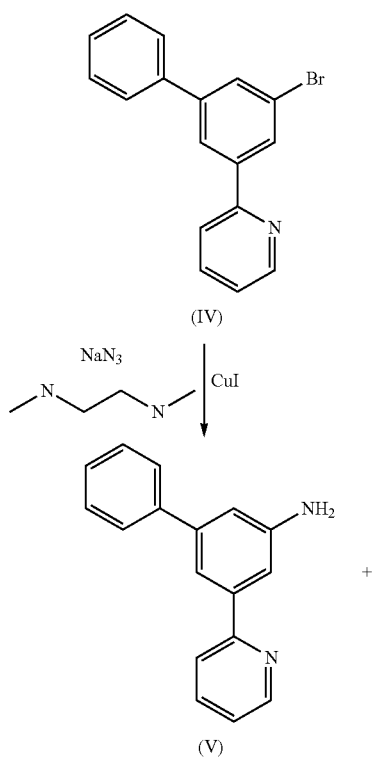

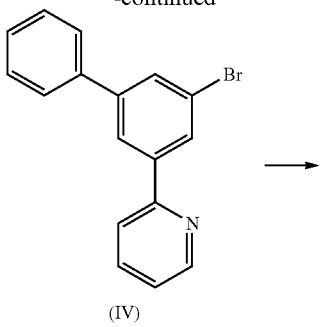

(IV)

(VI)

Preparation of Compound (V)

15.8 g (51.1 mmol) of compound (IV), 9.7 g (51.1 mmol) of copper iodide, 6.6 g (102.2 mmol) of sodium azide and 5.4 g (61.3 mmol) of N,N-dimethyl-ethane-1,2-diamine are stirred under reflux for 10 h in 300 mL of dimethylsulfoxide (DMSO). After cooling to room temperature, 200 mL of ethylacetate and 100 mL of a solution of saturated NH₄Cl are added to the reaction mixture. The organic phase is separated off, washed three times with 300 mL of water, dried over magnesium sulfate, filtered and subsequently evaporated to dryness. The residue is recrystallised from toluene and finally dried under reduced pressure. The yield is 11.1 g (44.9 mmol), corresponding to 88% of theory.

Preparation of Compound (VI)

10.5 g (34.1 mmol) of compound (IV) and 8.4 g (34.1 mmol) of compound (V) are suspended in 400 mL of toluene under Ar atmosphere. 380 mg (0.68 mmol) of 1,1-bis-(diphenyl-phosphino)-ferrocene and 150 mg (0.68 mmol) of Pd(OAc)₂ are added to the flask and stirred vigorously under Ar atmosphere, Then 3.9 g (40.9 mmol) of sodium t-butoxide is added to the flask under Ar. The reaction mixture is stirred under reflux for 24 h. After cooling to room temperature, the organic phase is separated off, washed three times with 100 mL of water, dried over magnesium sulfate, filtered and subsequently evaporated to dryness. The residue is purified by column chromatography on silica gel using a mixture of ethylacetate/heptane (1:2). The yield is 15.3 g (32.4 mmol), corresponding to 95% of theory.

Example 3

Preparation of Compound (VII)

Synthetic Procedure for the Preparation of Compound (VII)

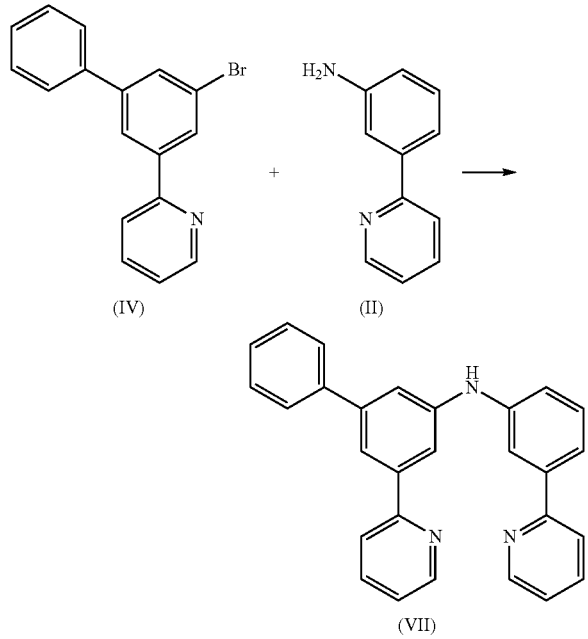

Preparation of Compound (VII)

10.5 g (34.1 mmol) of compound (IV) and 5.8 g (34.1 mmol) of compound (II) are suspended in 400 mL of toluene under Ar atmosphere. 380 mg (0.68 mmol) of 1,1-bis-(diphenyl-phosphino)-ferrocene and 150 mg (0.68 mmol) of $Pd(OAc)_2$ are added to the flask and stirred vigorously under Ar atmosphere. Then 3.9 g (40.9 mmol) of sodium t-butoxide is added to the flask under Ar. The reaction mixture is stirred under reflux for 24 h. After cooling, the organic phase is separated off, washed three times with 100 mL of water, dried over magnesium sulfate, filtered and subsequently evaporated to dryness. The residue is purified by column chromatography on silica gel using a mixture of ethylacetate/heptane (1:2). The yield is 11.1 g (27.9 mmol), corresponding to 82% of theory.

Example 4

Preparation of Compound (XII)

Synthetic Procedure for the Preparation of Compound (XII)

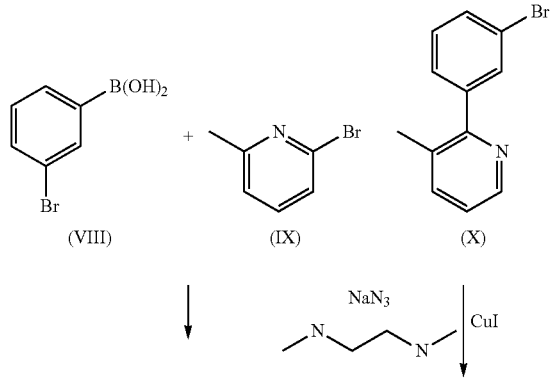

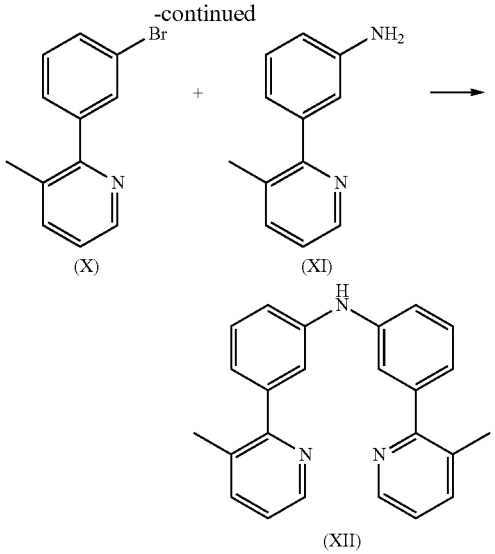

Preparation of Compound (X)

17.2 g (100.2 mmol) of compound (IX) and 20.5 g (120.2 mmol) of compound (VIII) and 16.8 g (120.2 mmol) of potassium carbonate are suspended in 600 mL of toluene and 200 mL of water. 1.1 g (1.0 mmol) of tetrakis(triphenyl-phosphine)palladium(0) are added to this suspension, and the reaction mixture is stirred under reflux for 16 h. After cooling, the organic phase is separated off, washed three times with 600 mL of water, dried over sodium sulfate and subsequently evaporated to dryness. The residue is purified by column chromatography using a mixture of ethylacetate/heptane (1:3). The yield is 21.6 g (87.2 mmol), corresponding to 86% of theory.

Preparation of Compound (XI)

21.6 g (87.2 mmol) of compound (X), 16.6 g (87.2 mmol) of copper iodide, 11.3 g (174.4 mmol) of sodium azide and 9.2 g (104.6 mmol) of N,N-dimethyl-ethane-1,2-diamine are stirred under reflux for 10 h in 500 mL of dimethylsulfoxide (DMSO). After cooling to room temperature, 200 mL of ethylacetate and 100 mL of a solution of saturated $NH_4Cl$ are added to the reaction mixture. The organic phase is separated off, washed three times with 300 mL of water, dried over magnesium sulfate, filtered and subsequently evaporated to dryness. The residue is recrystallised from toluene and finally dried under reduced pressure. The yield is 14.1 g (76.7 mmol), corresponding to 88% of theory.

Preparation of Compound (XII)

14.0 g (56.6 mmol) of compound (IV) and 10.4 g (56.6 mmol) of compound (XI) are suspended in 300 mL of toluene under Ar atmosphere. 620 mg (1.1 mmol) of 1,1-bis-(diphenylphosphino)-ferrocene and 250 mg (1.1 mmol) of $Pd(OAc)_2$ are added to the flask, stirred vigorously under Ar atmosphere then 6.5 g (68.0 mmol) of sodium t-butoxide is added to the flask under Ar. The reaction mixture is stirred under reflux for 24 h. After cooling to room temperature, the organic phase is separated off, washed three times with 200 mL of water, dried over magnesium sulfate, filtered and subsequently evaporated to dryness. The residue is purified by column chromatography on silica gel using a mixture of ethylacetate/heptane (1:2). The yield is 18.3 g (52.1 mmol), corresponding to 92% of theory.

Example 5

Preparation of Compound (XIV)

Synthetic Procedure for the Preparation of Compound (XIV)

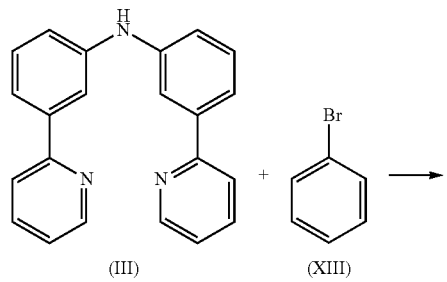

Preparation of Compound (XIV)

6.8 g (21.1 mmol) of compound (III) and 3.3 g (21.1 mmol) of compound (XIII) are suspended in 120 mL of toluene under Ar atmosphere. 94 mg (0.42 mmol) of Pd(OAc)$_2$ are added to the flask and stirred under Ar atmosphere then 0.8 mL of a 1 M tri-tert-butylphosphine solution and 2.4 g (25.4 mmol) of sodium t-butoxide are added to the flask. The reaction mixture is stirred under reflux for 24 h. After cooling, the organic phase is separated off, washed three times with 60 mL of water, dried over magnesium sulfate, filtered and subsequently evaporated to dryness. The residue is purified by column chromatography on silica gel using a mixture of ethylacetate/heptane (1:2). The yield is 8.0 g (20.0 mmol), corresponding to 95% of theory.

Comparative Example for Compound (XIV)

Routes Published

1) According to U.S. Pat. No. 7,442,792: 78% of overall yield

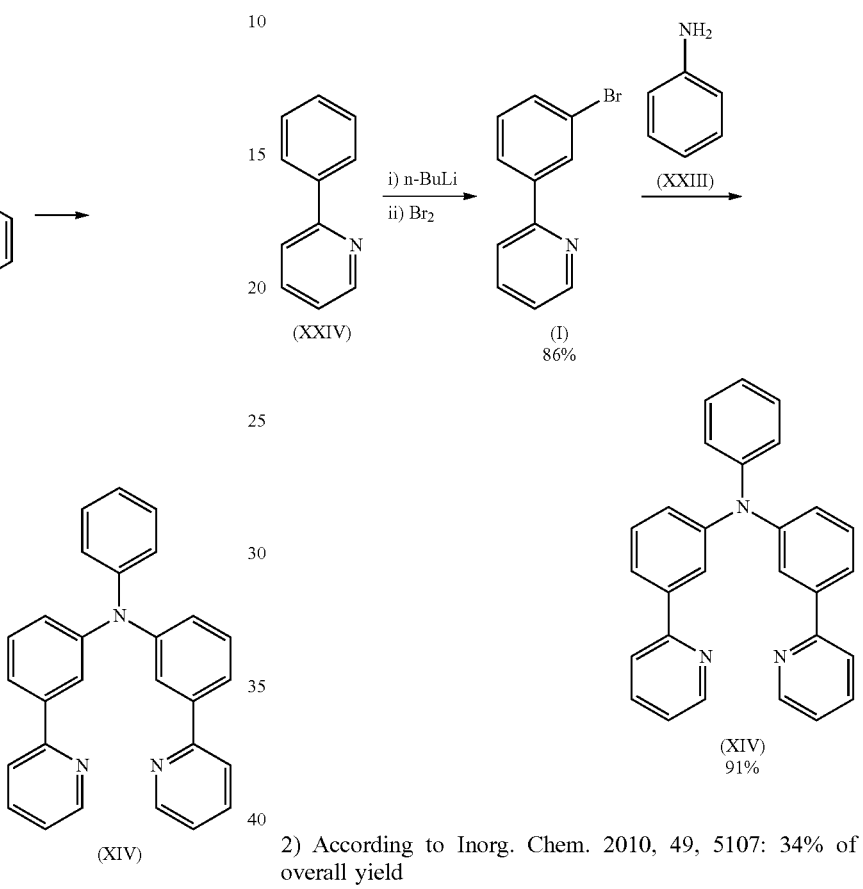

2) According to Inorg. Chem. 2010, 49, 5107: 34% of overall yield

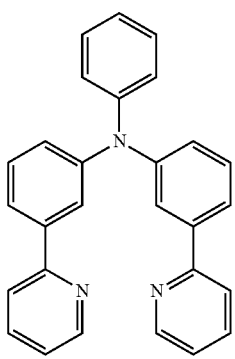

75%

Example 6

Preparation of Compound (XVI)

Synthetic Procedure for the Preparation of Compound (XVI)

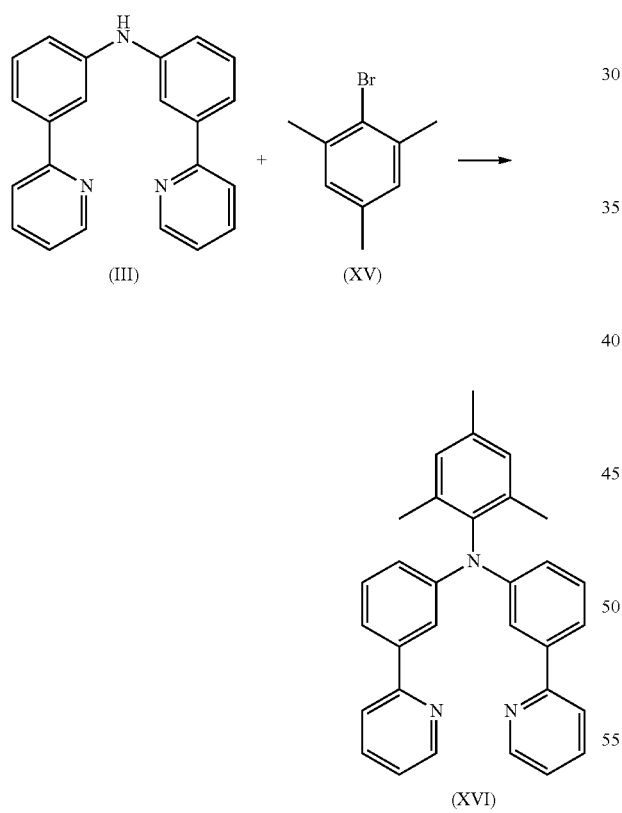

Preparation of Compound (XVI)

5.5 g (17.1 mmol) of compound (III) and 3.4 g (17.1 mmol) of compound (XIII) are suspended in 120 mL of toluene under Ar atmosphere. 76 mg (0.34 mmol) of Pd(OAc)$_2$ are added to the flask and stirred under Ar atmosphere then 0.7 mL of a 1 M tri-tert-butylphosphine solution and 2.0 g (20.5 mmol) of sodium t-butoxide are added to the flask under Argon. The reaction mixture is stirred under reflux for 24 h.

After cooling to room temperature, the organic phase is separated off, washed three times with 60 mL of water, dried over magnesium sulfate, filtered and subsequently evaporated to dryness. The residue is purified by column chromatography on silica gel using a mixture of ethylacetate/heptane (1:2). The yield is 6.8 g (15.4 mmol), corresponding to 90% of theory.

Comparative Example for Compound (XVI)

Route Published

1) According to U.S. Pat. No. 7,442,792: 52% of overall yield

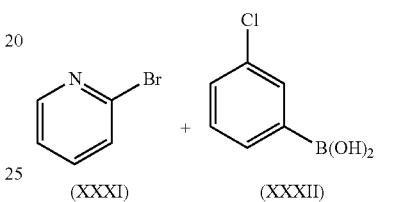

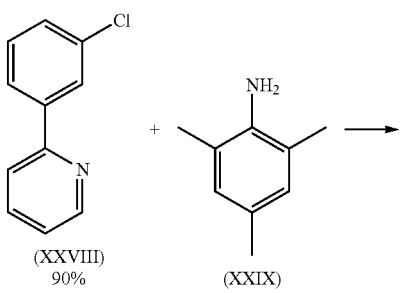

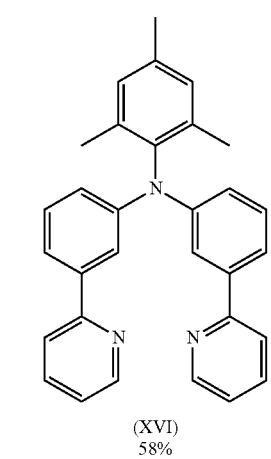

Example 7

Preparation of Compound (XVIII)

Synthetic Procedure for the Preparation of Compound (XVIII)

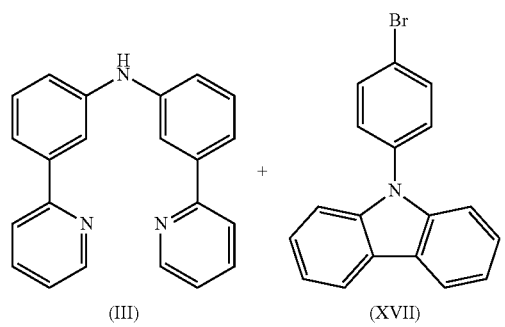

(III)  (XVII)

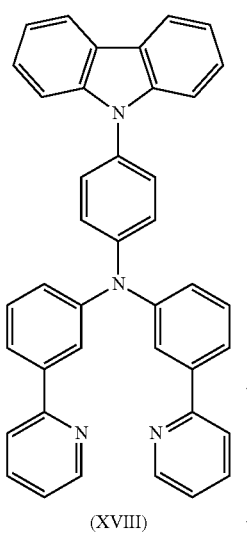

(XVIII)

Preparation of Compound (XVIII)

8.5 g (26.3 mmol) of compound (III) and 8.4 g (26.3 mmol) of compound (XVII) are suspended in 250 mL of toluene under Ar atmosphere. 118 mg (0.53 mmol) of Pd(OAc)$_2$ are added to the flask and stirred under Ar atmosphere then 1 mL of a 1 M tri-tert-butylphosphine solution and 3.0 g (31.5 mmol) of sodium t-butoxide are added to the flask under Argon. The reaction mixture is stirred under reflux for 24 h. After cooling to room temperature, the organic phase is separated off, washed three times with 60 mL of water, dried over magnesium sulfate, filtered and subsequently evaporated to dryness. The residue is purified by column chromatography on silica gel using a mixture of ethylacetate/heptane (1:2). The yield is 13.7 g (24.2 mmol), corresponding to 92% of theory.

Comparative Example for Compound (XVIII)

Route Published

1) According to U.S. Pat. No. 7,442,792: 67% of overall yield

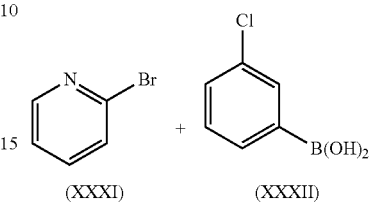

(XXXI)  (XXXII)

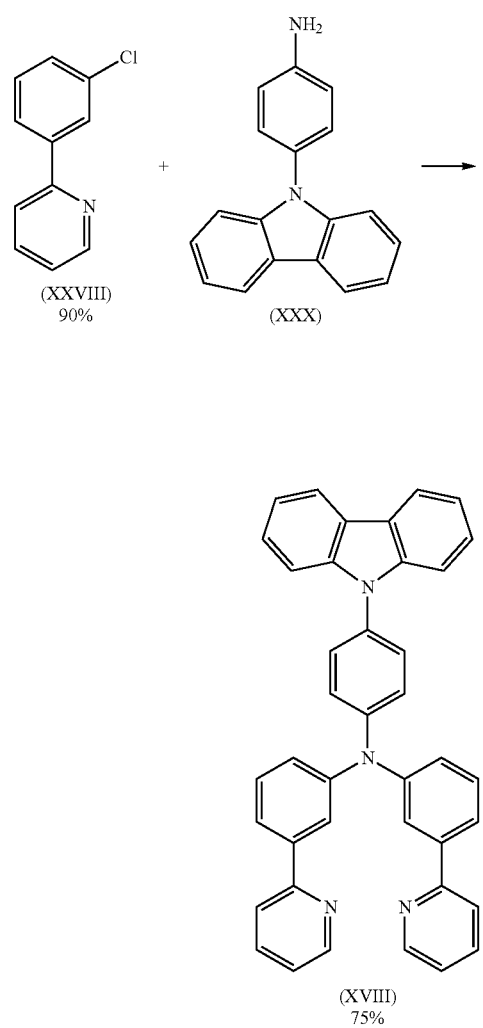

(XXVIII)
90%

(XXX)

(XVIII)
75%

Example 8

Preparation of Compound (XIX)

Synthetic Procedure for the Preparation of Compound (XIX)

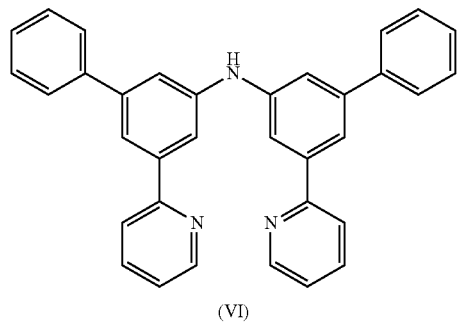

(VI)

+

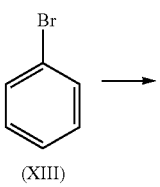

(XIII)

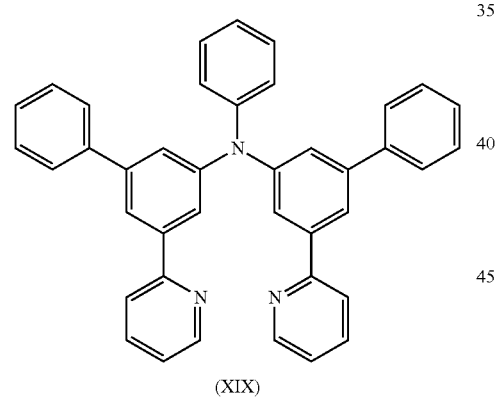

(XIX)

Preparation of Compound (XIX)

12.4 g (26.3 mmol) of compound (III) and 3.9 g (26.3 mmol) of compound (XIII) are suspended in 250 mL of toluene under Ar atmosphere. 118 mg (0.53 mmol) of Pd(OAc)$_2$ are added to the flask and stirred under Ar atmosphere then 1 mL of a 1 M tri-tert-butylphosphine solution and 3.0 g (31.5 mmol) of sodium t-butoxide are added to the flask under Argon. The reaction mixture is stirred under reflux for 24 h. After cooling to room temperature, the organic phase is separated off, washed three times with 60 mL of water, dried over magnesium sulfate, filtered and subsequently evaporated to dryness. The residue is purified by column chromatography on silica gel using a mixture of ethylacetate/heptane (1:2). The yield is 13.1 g (23.7 mmol), corresponding to 90% of theory.

Comparative Example for Compound (XIX)

Route Published

According to U.S. Pat. No. 7,442,792: 28% of overall yield

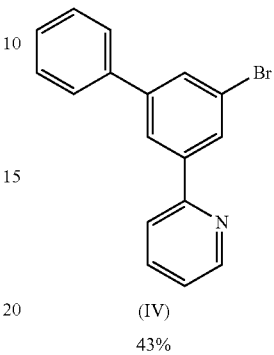

(IV)    (XXIII)
43%

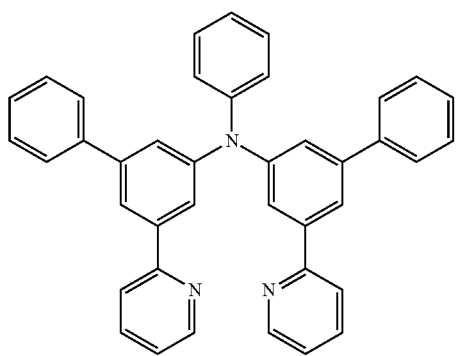

(XIX)
65%

Example 9

Preparation of Compound (XX)

Synthetic Procedure for the Preparation of Compound (XX)

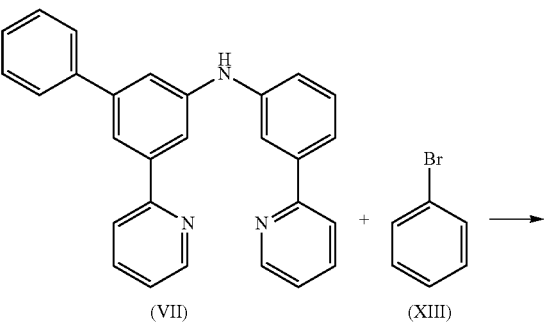

(VII)    (XIII)

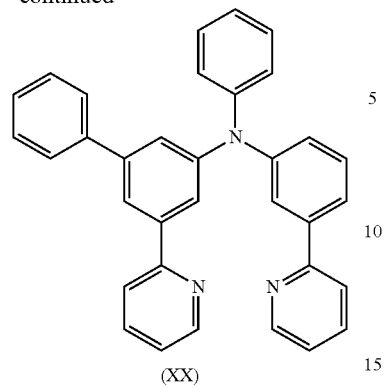

(XX)

Preparation of Compound (XX)

9.2 g (23.2 mmol) of compound (VII) and 3.6 g (23.2 mmol) of compound (XIII) are suspended in 150 mL of toluene under Ar atmosphere. 104 mg (0.46 mmol) of Pd(OAc)$_2$ are added to the flask and stirred under Ar atmosphere then 0.9 mL of a 1 M tri-tert-butylphosphine solution and 2.7 g (27.9 mmol) of sodium t-butoxide are added to the flask under Argon. The reaction mixture is stirred under reflux for 24 h. After cooling to room temperature, the organic phase is separated off, washed three times with 60 mL of water, dried over magnesium sulfate, filtered and subsequently evaporated to dryness. The residue is purified by column chromatography on silica gel using a mixture of ethylacetate/heptane (1:2). The yield is 10.4 g (21.8 mmol), corresponding to 94% of theory.

Comparative Example for Compound (XX)

Preparation of Comparative Compound (XX)

Synthetic Procedure for the Preparation of Compound (XX)

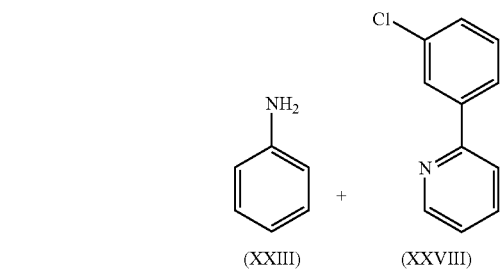

(XXIII)  (XXVIII)

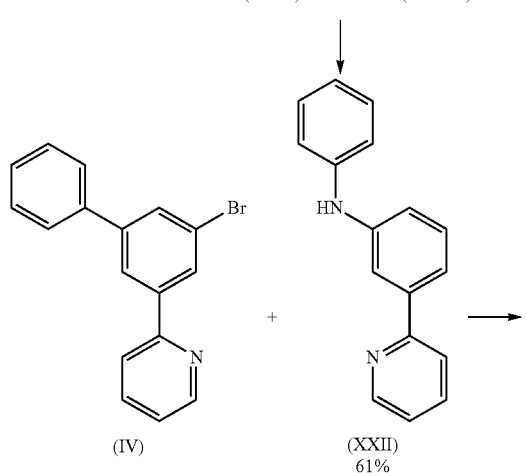

(IV)  (XXII)
       61%

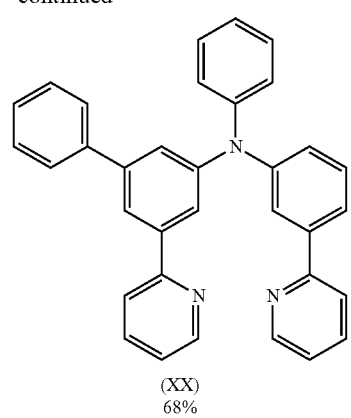

(XX)
68%

Preparation of Compound (XX)

7.9 g (25.6 mmol) of compound (IV) and 6.3 g (25.6 mmol) of compound (XXII) are suspended in 200 mL of toluene under Ar atmosphere. 115 mg (0.51 mmol) of Pd(OAc)$_2$ are added to the flask and stirred under Ar atmosphere then 1.0 mL of a 1 M tri-tert-butylphosphine solution and 2.9 g (30.7 mmol) of sodium t-butoxide are added to the flask under Ar. The reaction mixture is stirred under reflux for 24 h. After cooling to room temperature, the organic phase is separated off, washed three times with 50 mL of water, dried over magnesium sulfate, filtered and subsequently evaporated to dryness. The residue is purified by column chromatography on silica gel using a mixture of ethylacetate/heptane (1:2). The yield is 8.3 g (17.4 mmol), corresponding to 68% of theory.

Example 10

Preparation of Compound (XXI)

Synthetic Procedure for the Preparation of Compound (XXI)

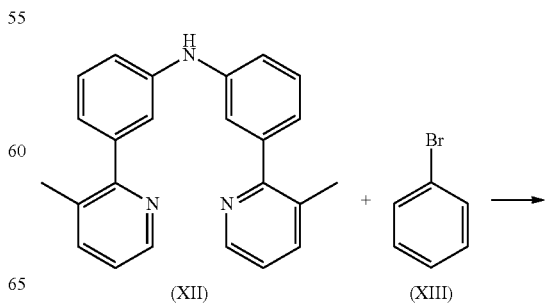

(XII)  (XIII)

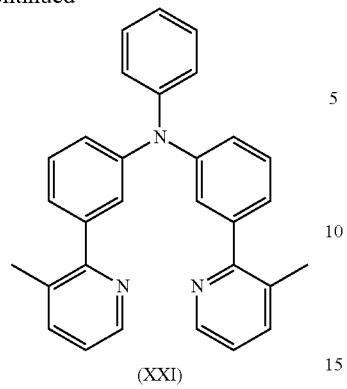

(XXI)

Preparation of Compound (XXI)

25.5 g (72.6 mmol) of compound (XII) and 3.2 g (72.6 mmol) of compound (XIII) are suspended in 300 mL of toluene under Ar atmosphere. 325 mg (1.45 mmol) of Pd(OAc)$_2$ are added to the flask and stirred under Ar atmosphere then 2.9 mL of a 1 M tri-tert-butylphosphine solution and 8.4 g (87.2 mmol) of sodium t-butoxide are added to the flask under Ar. The reaction mixture is stirred under reflux for 24 h. After cooling to room temperature, the organic phase is separated off, washed three times with 200 mL of water, dried over magnesium sulfate, filtered and subsequently evaporated to dryness. The residue is purified by column chromatography on silica gel using a mixture of ethylacetate/heptane (1:2). The yield is 34.6 g (81.1 mmol), corresponding to 93% of theory.

Comparative Example for Compound (XXI)

Synthetic Procedure for the Preparation of Compound (XXI)

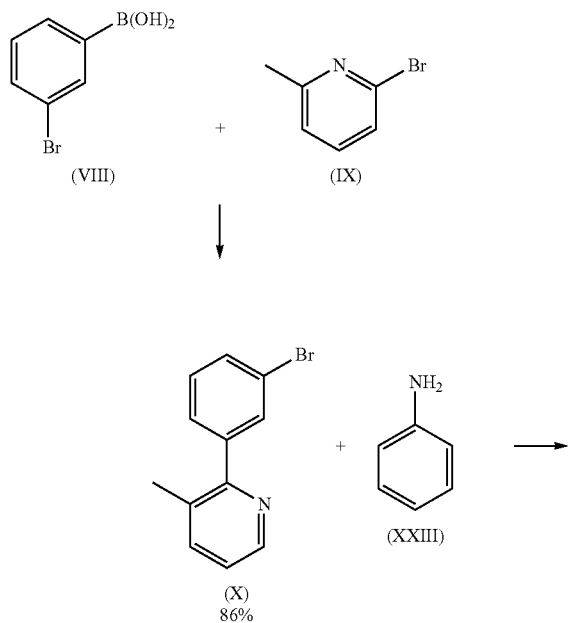

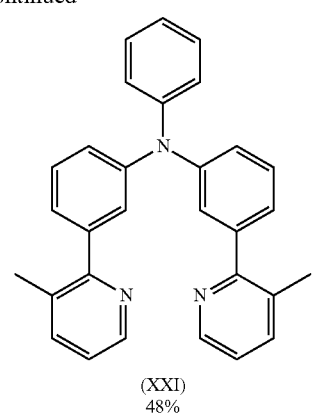

(XXI)
48%

Preparation of Compound (XXI)

16.9 g (68.2 mmol) of compound (X) and 3.2 g (34.1 mmol) of compound (XXIII) are suspended in 150 mL of toluene under Ar atmosphere. 380 mg (0.68 mmol) of Pd(OAc)$_2$ are added to the flask and stirred under Ar atmosphere then 1.4 mL of a 1 M tri-tert-butylphosphine solution and 7.9 g (82.1 mmol) of sodium t-butoxide are added to the flask under Ar. The reaction mixture is stirred under reflux for 24 h. After cooling to room temperature, the organic phase is separated off, washed three times with 50 mL of water, dried over magnesium sulfate, filtered and subsequently evaporated to dryness. The residue is purified by column chromatography on silica gel using a mixture of ethylacetate/heptane (1:2). The yield is 5.7 g (16.4 mmol), corresponding to 48% of theory.

The following Tables 1 and 2 summarize the results.

TABLE 1

Last step yield

| Compound | Yield (Prior art) | Yield (according to the present invention) |
|---|---|---|
| (XIV) | 91%[1] 75%[2] | 95% |
| (XVI) | 58%[1] | 90% |
| (XVIII) | 75%[1] | 92% |
| (XIX) | 65%[1] | 90% |
| (XX) | 68%[3] | 94% |
| (XXI) | 48%[3] | 93% |

[1] U.S. Pat. No. 7,442,792;
[2] Inorg. Chem. 2010, 49, 5107;
[3] Preparation of comparative compounds

TABLE 2

Overall yield

| Compound | Overall Yield (prior art) | Overall Yield (according to the present invention) |
|---|---|---|
| (XIV) | 78%[1] 33%[2] | 91% |
| (XVI) | 52%[1] | 75% |
| (XVIII) | 68%[1] | 88% |

TABLE 2-continued

| | Overall yield | |
|---|---|---|
| Compound | Overall Yield (prior art) | Overall Yield (according to the present invention) |
| (XIX) | 28%[1] | 75% |
| (XX) | 41%[3] | 77% |
| (XXI) | 41%[3] | 65% |

[1]U.S. Pat. No. 7,442,792;
[2]Inorg. Chem. 2010, 49, 5107;
[3]Preparation of comparative compound

The invention claimed is:

1. A method for preparing a secondary amine (P) comprising reacting a compound (E1) and a primary amine (E2), wherein E1 is a compound of formula (13), E2 is a compound of formula (14) and P is a compound of formula (15):

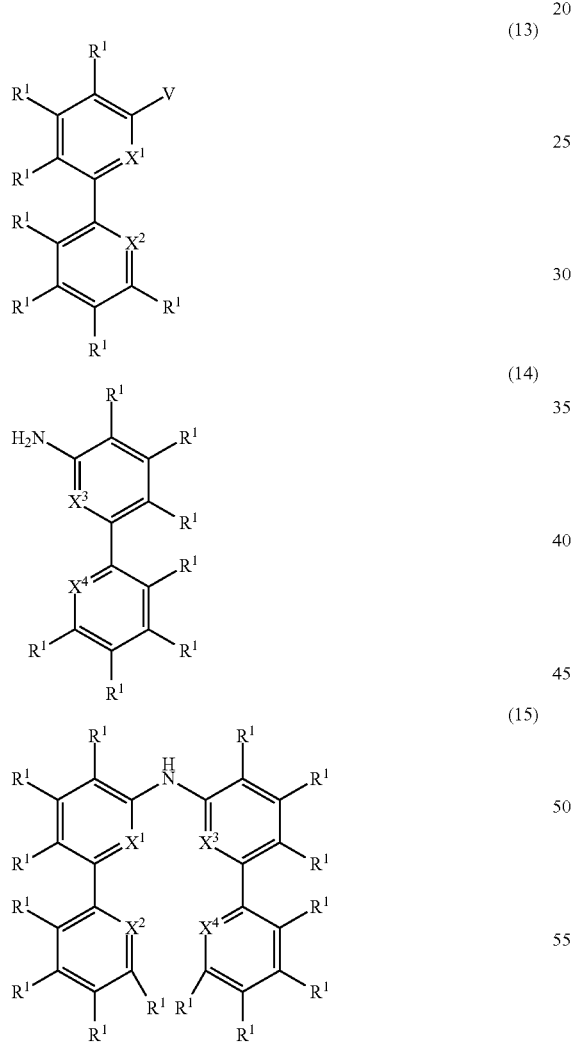

wherein
$X^1$ is C, $X^2$ is N, $X^3$ is C, and $X^4$ is N, or
$X^1$ is N, $X^2$ is C, $X^3$ is C, and $X^4$ is N, or
$X^1$ is C, $X^2$ is N, $X^3$ is N, and $X^4$ is C, or
$X^1$ is C, $X^2$ is C, $X^3$ is N, and $X^4$ is N,
wherein C is a carbon atom and N is a nitrogen atom;
V is a leaving group;

$R^1$ is, identically or differently on each occurrence, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, $B(R^2)_2$, a straight-chain alkyl, alkoxy, or thioalkoxy group having 1 to 40 C atoms or a straight-chain alkenyl or alkynyl group having 2 to 40 C atoms or a branched or cyclic alkyl, alkenyl, alkynyl, alkoxy, or thioalkoxy group having 3 to 40 C atoms, each of which are optionally substituted by one or more $R^2$, wherein one or more non-adjacent $CH_2$ groups are optionally replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S, or $CONR^2$ and wherein one or more H atoms are optionally replaced by D, F, Cl, Br, I, CN, or $NO_2$, an aromatic or heteroaromatic ring system having 5 to 60 aromatic ring atoms optionally substituted by one or more $R^2$, an aryloxy or heteroaryloxy group having 5 to 60 aromatic ring atoms optionally substituted by one or more $R^2$, a diarylamino group, diheteroarylamino group, or arylheteroarylamino group having 10 to 40 aromatic ring atoms optionally substituted by one or more $R^2$, or a combination of two or more of these groups; and wherein two or more $R^1$ optionally define a mono- or polycyclic, aliphatic, aromatic, and/or benzo-fused ring system with one another;

$R^2$ is, identically or differently on each occurrence, H, D, F, Cl, Br, I, $N(R^3)_2$, CN, $NO_2$, $Si(R^3)_3$, $B(OR^3)_2$, $C(=O)R^3$, $P(=O)(R^3)_2$, $S(=O)R^3$, $S(=O)_2R^3$, $OSO_2R^3$, a straight-chain alkyl, alkoxy, or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which are optionally substituted by one or more $R^3$, wherein one or more non-adjacent $CH_2$ groups are optionally replaced by $R^3C=CR^3$, $C\equiv C$, $Si(R^3)_2$, $Ge(R^3)_2$, $Sn(R^3)_2$, $C=O$, $C=S$, $C=Se$, $C=NR^3$, $P(=O)(R^3)$, SO, $SO_2$, $NR^3$, O, S, or $CONR^3$ and wherein one or more H atoms are optionally replaced by D, F, Cl, Br, I, CN, or $NO_2$, an aromatic or heteroaromatic ring system having 5 to 60 aromatic ring atoms optionally substituted by one or more radicals $R^3$, an aryloxy or heteroaryloxy group having 5 to 60 aromatic ring atoms, optionally substituted by one or more $R^3$, a diarylamino group, diheteroarylamino group, or arylheteroarylamino group having 10 to 40 aromatic ring atoms optionally substituted by one or more radicals $R^3$, or a combination of two or more of these groups; and wherein two or more adjacent radicals $R^2$ optionally define a mono- or polycyclic, aliphatic, or aromatic ring system with one another; and $R^3$ is, identically or differently on each occurrence, H, D, F, or an aliphatic, aromatic, and/or heteroaromatic hydrocarbon radical having 1 to 20 C atoms, wherein one or more H atoms are optionally replaced by F; and wherein two or more substituents $R^3$ optionally define a mono- or polycyclic, aliphatic, or aromatic ring system with one another.

2. The method of claim 1, wherein E1 is a compound of formula (34), E2 is a compound of formula (35), and P is a compound of formula (36):
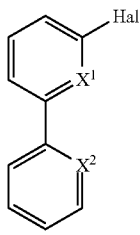 (34)
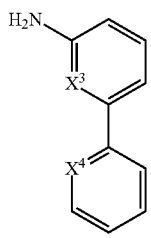 (35)
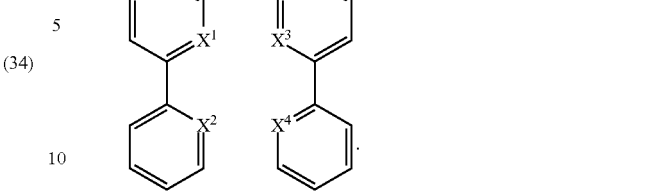 (36)
3. A method for preparing a compound for use as a ligand for metal complexes comprising reacting the compound P of claim 1 with a halide of formula $R^1$-Hal to obtain a compound having the following formula:
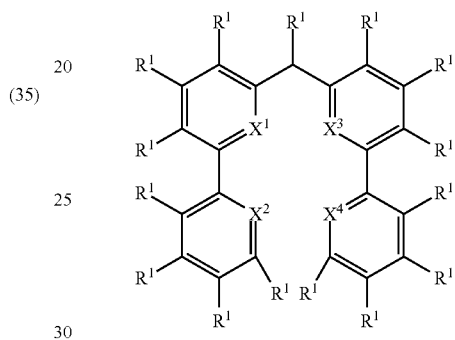
wherein the reaction is a Buchwald reaction.
* * * * *